(12) United States Patent
Chan et al.

(10) Patent No.: US 7,312,876 B2
(45) Date of Patent: Dec. 25, 2007

(54) OPTICAL IMAGE MEASURING APPARATUS

(75) Inventors: Kinpui Chan, Yamagata (JP); Masahiro Akiba, Yamagata (JP)

(73) Assignee: Kabushiki Kaisha Topcon, Tokyo (JP)

( * ) Notice: Subject to any disclaimer, the term of this patent is extended or adjusted under 35 U.S.C. 154(b) by 234 days.

(21) Appl. No.: 11/246,395

(22) Filed: Oct. 11, 2005

(65) Prior Publication Data

US 2006/0082781 A1 Apr. 20, 2006

(30) Foreign Application Priority Data

Oct. 14, 2004 (JP) ............................. 2004-299600

(51) Int. Cl.
*G01B 9/02* (2006.01)
*G01B 11/02* (2006.01)
(52) U.S. Cl. ...................... 356/487; 356/497; 356/495
(58) Field of Classification Search .................... None
See application file for complete search history.

(56) References Cited

U.S. PATENT DOCUMENTS

| 6,900,899 | B2 * | 5/2005 | Nevis ......................... 356/484 |
| 7,038,788 | B2 * | 5/2006 | Matsumoto ................. 356/484 |
| 7,145,661 | B2 * | 12/2006 | Hitzenberger ............... 356/497 |
| 2006/0028652 | A1 * | 2/2006 | Chan et al. .................. 356/497 |

FOREIGN PATENT DOCUMENTS

JP 2004-105708 4/2004

OTHER PUBLICATIONS

N. Tanno; "The imaging technic of the optical coherence tomography and its application to living organism image;" *Kogaku* (*Japanese Journal of Optics*); vol. 28; No. 3; 1999; pp. 116-125 and Cover page (11 Sheets total)./Discussed in the specification.

T. Nakajima; "Principle and application of the optical heterodyne method;" *Optical Heterodyne Technology*; 2003; pp. 1-10 and Cover page (7 Sheets total)./Discussed in the specification.

K.P. Chan, et al; "Micrometre-resolution, optical imaging of objects through highly scattered media using a heterodyne detector array;" *Electronics Letters*; vol. 30; No. 21; Oct. 13, 1994; pp. 1753-1754./Discussed in the specification.

* cited by examiner

*Primary Examiner*—Gregory J. Toatley, Jr.
*Assistant Examiner*—Jonathan Skovholt
(74) *Attorney, Agent, or Firm*—Edwards Angell Palmer & Dodge LLP

(57) ABSTRACT

An optical image measuring apparatus capable of measuring an object to be measured which includes a birefringent layer in a short time is provided. The optical image measuring apparatus includes a broad-band light source, lenses for increasing a diameter of the light beam, a polarizing plate, a half mirror, a wavelength plate for converting the reference light to circularly polarized light, a wavelength plate for converting the signal light to circularly polarized light and converting the signal light to linearly polarized light, a frequency shifter, a polarization beam splitter for separating an S-polarized light component and a P-polarized light component from interference light, CCDs for receiving the respective polarized light components and outputting detection signals each including intensity change information, and a signal processing portion for forming an image reflecting a birefringent property, of an object to be measured based on the intensity change information.

49 Claims, 8 Drawing Sheets

OPTICAL IMAGE MEASURING APPARATUS

BACKGROUND OF THE INVENTION

1. Field of the Invention

The present invention relates to an optical image measuring apparatus that applies a light beam to an object to be measured, particularly a light scattering medium, and produces a surface form or inner form of the object to be measured by detecting a reflected light beam or a transmitted light beam. In particular, the present invention relates to an optical image measuring apparatus for measuring the surface form or inner form of the object to be measured by using an optical heterodyne detection method to produce the image of the measured form.

2. Description of the Related Art

In recent years, attention has been given to optical imaging technique that produces an image of a surface or inner portion of an object to be measured using a laser light source or the like. This optical imaging technique is not hazardous to human bodies in contrast to the conventional X-ray CT. Therefore, the development of applications in the medical field has been particularly expected.

An example of a typical method of the optical imaging technique is a low coherent interference method (also called 'optical coherence tomography' or the like). This method uses the low coherence of a broad-band light source having a broad spectral width, such as a super luminescent diode (SLD). According to this method, reflection light from an object to be measured or light transmitted therethrough can be detected at superior distance resolution on the order of $\mu m$ (for example, see Naohiro Tanno, "Kogaku" (Japanese Journal of Optics), Volume 28, No. 3, 116 (1999)).

FIG. 7 shows a basic structure of a conventional optical image measuring apparatus based on a Michelson interferometer, as an example of an apparatus using the low coherent interference method. An optical image measuring apparatus 300 includes a broad-band light source 301, a mirror 302, a beam splitter 303, and a photo detector 304. An object to be measured 305 is made of a scattering medium. A light beam from the broad-band light source 301 is divided by the beam splitter 303 into two, that is, reference light R propagating to the mirror 302 and signal light S propagating to the object to be measured 305. The reference light R is light reflected by the beam splitter 303. The signal light S is light transmitted through the beam splitter 303.

Here, as shown in FIG. 7, a propagating direction of the signal light S is set as a z-axis direction and a plane orthogonal to the propagating direction of the signal light S is defined as an x-y plane. The mirror 302 is movable in a direction indicated by a double-headed arrow in FIG. 7 (z-scanning direction).

The reference light R is subjected to a Doppler frequency shift through when reflected by the z-scanning mirror 302. On the other hand, the signal light S is reflected from the surface of the object to be measured 305 and from the inner layers thereof when the object to be measured 305 is irradiated with the signal light S. The object to be measured 305 is made of the scattering medium, so reflection light of the signal light S may be a diffusing wave having random phases. The signal light propagating through the object to be measured 305 and the reference light that propagates through the mirror 302 to be subjected to the frequency shift are superimposed on each other by the beam splitter 303 to produce interference light.

In the image measurement using such a low coherent interference method, interference occurs only when a difference in optical path length between the signal light S and the reference light R is within the coherence length (coherent distance) on the order of $\mu m$ of the light source. In addition, only the component of the signal light S whose phase is correlated to that of the reference light R interferes with the reference light R. That is, only the coherent signal light component of the signal light S selectively interferes with the reference light R. Based on their principles, the position of the mirror 302 is shifted by the z-scanning to vary the optical path length of the reference light R, so that a reflectance profile of the inner layers of the object to be measured 305 is measured. The object to be measured 305 is also scanned with the irradiated signal lights in an x-y plane direction. The interference light is detected by the photo detector 304 during such scanning in the z-direction and the x-y plane direction. An electrical signal (heterodyne signal) outputted as a detection result is analyzed to obtain a two-dimensional sectional image of the object to be measured 305 (see Naohiro Tanno, "Kogaku" (Japanese Journal of Optics), Volume 28, No. 3, 116 (1999)).

Assume that an intensity of the reference light R and an intensity of the signal light S which are superimposed by the beam splitter 303 are given by $I_r$ and $I_s$, respectively, and a frequency difference between the reference light R and the signal light S and a phase difference therebetween are given by $f_{if}$ and $\Delta\theta$, respectively. In this case, a heterodyne signal as expressed by the following expression is outputted from the photo detector (for example, see Yoshizawa and Seta "Optical Heterodyne Technology (revised edition)", New Technology Communications (2003), p. 2).

Expression (1)

$$i(t) \propto I_r + I_s + 2\sqrt{I_r I_s} \cos(2\pi f_{if} t + \Delta\theta) \qquad (1)$$

The third term of the right side of the expression (1) indicates an alternating current electrical signal and the frequency $f_{if}$ thereof is equal to the frequency of beat caused from the interference between the reference light R and the signal light S. The frequency $f_{if}$ of an alternating current component of the heterodyne signal is called a beat frequency or the like. The first and second terms of the right side of the expression (1) indicate the direct current components of the heterodyne signal and correspond to a signal intensity of background light of interference light.

However, when the two-dimensional cross sectional image is obtained by the conventional low coherent interference method, it is necessary to scan the object to be measured 305 with a light beam and to successively detect reflection light waves from respective regions of the object to be measured 305 in a depth direction (z-direction) and a sectional direction (x-y plane direction). Therefore, the measurement of the object to be measured 305 is needed to be carried out in a wide range for instance by scanning the signal light and requires a long time. In addition, it is hard to shorten a measurement time in view of measurement fundamentals.

In views of such problems, an optical image measuring apparatus for shortening a measurement time has been proposed. FIG. 8 shows a fundamental structure of an example of such an apparatus. As shown in FIG. 8, an optical image measuring apparatus 400 includes a broad-band light source 401, a mirror 402, a beam splitter 403, a two-dimensional photo sensor array 404 serving as a photo detector, and lenses 406 and 407. A light beam emitted from the light source 401 is converted into a parallel light flux by the lenses 406 and 407 and a beam diameter thereof is widened thereby. Then, the parallel light flux is divided into two, that is, the reference light R and the signal light S by the beam splitter 403. The reference light R is subjected to Doppler frequency shift through z-scanning with the mirror 402. On the other hand, the signal light S is incident on the object to be measured 405 over a broad area of the x-y plane because the beam diameter is widened. Therefore, the signal light S becomes reflection light including information related to the surface and inner portion of the object to be measured 405 over a wide area. The reference light R and the signal light S are superimposed on each other by the beam splitter 403 and detected by elements (photo sensors) arranged in parallel on the two-dimensional photo sensor array 404. Thus, it is possible to obtain a two-dimensional cross sectional image of the object to be measured 405 in real time without light beam scanning.

An apparatus described in K. P. Chan, M. Yamada, and H. Inaba, "Electronics Letters", Vol. 30, 1753 (1994) has been known as such a non-scanning type optical image measuring apparatus. In the apparatus described in the same document, a plurality of heterodyne signals outputted from a two-dimensional photo sensor array are inputted to signal processing systems arranged in parallel to detect the amplitude and phase of each of the heterodyne signals.

An optical image measuring apparatus is applied to measurement on an object to be measured which includes a birefringent layer such as a retinal nerve fibre layer (RNFL) of an eye (for example, see JP 2004-105708 A (claims 16, 32, and 49 to 56, specification paragraphs [0019], [0100] to [0108], and FIG. 11).

In the optical image measuring apparatus described in JP 2004-105708A, light from a light source is polarized in a longitudinal direction by a polarizer and allowed to enter a fiber. A ¼-wavelength delay plate (¼-wavelength plate) is provided on each of an optical path of signal light and an optical path of reference light. Interference light produced from the signal light and the reference light is separated into two polarized components orthogonal to each other by a polarization beam splitter to detect the respective polarized components. The detected two polarized components are combined with each other to obtain information related to the birefringent layer, thereby forming an image.

However, in order to obtain an image reflecting a birefringent property, of the object to be measured over a wide range using the optical image measuring apparatus described in JP 2004-105708 A, it is necessary to scan the object to be measured with the signal light as in the case using the apparatus shown in FIG. 7. Therefore, there is a problem in that a measurement time is prolonged.

SUMMARY OF THE INVENTION

The present invention has been made in view of the above-mentioned circumstances. An object of the present invention is to provide an optical image measuring apparatus capable of effectively measuring an object to be measured which includes a birefringent layer in a short time.

In order to achieve the above object, there is provided an optical image measuring apparatus according to a first aspect of the present invention, including: light beam outputting means for outputting a light beam whose intensity is periodically modulated; beam diameter increasing means for increasing a beam diameter of the light beam; linear polarization means for converting a polarization characteristic of the light beam to linear polarization; light beam dividing means for dividing the light beam whose beam diameter is increased and polarization characteristic is converted to the linear polarization into signal light propagating to an object to be measured and reference light propagating to a reference object; reference light polarizing means for converting a polarization characteristic of the reference light which is linearly polarized light; signal light polarizing means for converting a polarization characteristic of the signal light which is linearly polarized light before the signal light propagates through the object to be measured and converting to linear polarization the polarization characteristic of the signal light after the signal light propagates through the object to be measured; frequency shifting means for shifting a frequency of the signal light and a frequency of the reference light relative to each other; superimposing means for superimposing the reference light whose polarization characteristic is converted by the reference light polarizing means and the signal light which is converted to linearly polarized light by the signal light polarizing means on each other to produce interference light, the frequency of the signal light and the frequency of the reference light being shifted relative to each other by the frequency shifting means; interference light separating means for separating a plurality of polarized light components which are different from each other from the produced interference light; detecting means for receiving the polarized light components separated from the interference light and outputting a detection signal including intensity change information of each of the polarized light components; and signal processing means for forming an image reflecting a birefringent property, of the object to be measured based on the intensity change information of each of the polarized light components included in the outputted detection signal.

According to a second aspect of the present invention, there is provided an optical image measuring apparatus according to the first aspect of the invention, in which: the linear polarization means converts the light beam to linearly polarized light in an angle direction of 45° relative to an x-axis and a y-axis of an xy-plane orthogonal to a propagating direction of the light beam; and the signal light polarizing means converts to circularly polarized light the signal light which is the linearly polarized light in the angle direction of 45° before the signal light propagates through the object to be measured and converts to linearly polarized light the signal light which is the circularly polarized light after the signal light propagates through the object to be measured.

According to a third aspect of the present invention, there is provided an optical image measuring apparatus according to the second aspect of the invention, in which: the light beam dividing means and the superimposing means integrally compose a half mirror tilted relative to an optical path of the light beam outputted from the light beam outputting means, an optical path of the signal light, and an optical path of the reference light; and the signal light polarizing means includes a ¼-wavelength plate located between the half mirror and the object to be measured.

According to a fourth aspect of the present invention, there is provided an optical image measuring apparatus according to any one of the first to third aspects of the invention, in which: the linear polarization means converts the light beam to linearly polarized light in an angle direction of 45° relative to an x-axis and a y-axis of an xy-plane orthogonal to a propagating direction of the light beam; and the reference light polarizing means converts the reference light which is the linearly polarized light in the angle direction of 45° to circularly polarized light.

According to a fifth aspect of the present invention, there is provided an optical image measuring apparatus according to the fourth aspect of the invention, in which: the light beam dividing means and the superimposing means integrally compose a half mirror tilted relative to an optical path of the light beam outputted from the light beam outputting means, an optical path of the signal light, and an optical path of the reference light; and the reference light polarizing means includes a ⅛-wavelength plate located between the half mirror and the reference object.

According to a sixth aspect of the present invention, there is provided an optical image measuring apparatus according to any one of the second to fifth aspects of the invention, in which the linear polarization means includes a polarizing plate for transmitting an oscillation component of the light beam in the angle direction of 45°.

According to a seventh aspect of the present invention, there is provided an optical image measuring apparatus according to any one of the first to sixth aspects of the invention, in which the interference light separating means separates a P-polarized light component and an S-polarized light component which are orthogonal to each other from the interference light.

According to an eighth aspect of the present invention, there is provided an optical image measuring apparatus according to any one of the first to seventh aspects of the invention, in which the light beam outputting means includes: pulse generating means for generating a pulse signal having a frequency synchronized with frequency shift caused by the frequency shifting means; and a light source for outputting a pulsed light beam, which is driven based on the pulse signal.

According to a ninth aspect of the present invention, there is provided an optical image measuring apparatus according to the eighth aspect of the invention, in which the pulse generating means includes: a laser light source for emitting laser light; an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light; auxiliary detection means for detecting the produced auxiliary interference light and outputting an electrical signal having a frequency substantially equal to a beat frequency of the detected auxiliary interference light; and light source driving means for generating the pulse signal having the frequency synchronized with the frequency of the electrical signal outputted from the auxiliary detection means and outputting the generated pulse signal to the light source.

According to a tenth aspect of the present invention, there is provided an optical image measuring apparatus according to the first to seventh aspects of the invention, in which the light beam outputting means includes a light source for emitting a continuous light beam, and shutter means for periodically cutting off the emitted continuous light beam.

According to an eleventh aspect of the present invention, there is provided an optical image measuring apparatus according to the tenth aspect of the invention, in which the light beam means includes: a laser light source for emitting laser light; an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light; auxiliary detection means for detecting the produced auxiliary interference light and outputting an electrical signal having a frequency substantially equal to a beat frequency of the auxiliary interference light; and shutter driving means for generating a pulse signal having a frequency synchronized with the frequency of the electrical signal outputted from the auxiliary detection means and outputting the generated pulse signal to the shutter means, and in which the shutter means is driven based on the pulse signal outputted from the shutter driving means and periodically cuts off the continuous light beam emitted from the light source.

According to a twelfth aspect of the present invention, there is provided an optical image measuring apparatus including: a light source for continuously outputting a light beam; beam diameter increasing means for increasing a beam diameter of the light beam; linear polarization means for converting a polarization characteristic of the light beam to linear polarization; light beam dividing means for dividing the light beam whose beam diameter is increased and polarization characteristic is converted to the linear polarization into signal light propagating to an object to be measured and reference light propagating to a reference object; reference light polarizing means for converting a polarization characteristic of the reference light which is linearly polarized light; signal light polarizing means for converting a polarization characteristic of the signal light which is linearly polarized light before the signal light propagates through the object to be measured and converting to linear polarization the polarization characteristic of the signal light after the signal light propagates through the object to be measured; frequency shifting means for shifting a frequency of the signal light and a frequency of the reference light relative to each other; superimposing means for superimposing the reference light whose polarization characteristic is converted by the reference light polarizing means and the signal light which is converted to linearly polarized light by the signal light polarizing means on each other to produce interference light, the frequency of the signal light and the frequency of the reference light being shifted relative to each other by the frequency shifting means; interference light separating means for separating a plurality of polarized light components which are different from each other from the produced interference light; one intensity modulating means for periodically modulating intensities of the polarized light components separated from the interference light; one detecting means for receiving the polarized light components whose intensities are periodically modulated and outputting a detection signal including intensity change information of each of the polarized light components; and signal processing means for forming an image reflecting a birefringent property, of the object to be measured based on the intensity change information of each of the polarized light components included in the outputted detection signal.

According to a thirteenth aspect of the present invention, an optical image measuring apparatus includes: a light source for continuously outputting a light beam; beam diameter increasing means for increasing a beam diameter of the light beam; linear polarization means for converting a polarization characteristic of the light beam to linear polarization; light beam dividing means for dividing the light beam whose beam diameter is increased and polarization characteristic is converted to the linear polarization into signal light propagating to an object to be measured and reference light propagating to a reference object; signal light polarizing means for converting a polarization characteristic of the signal light which is linearly polarized light before the signal light propagates through the object to be measured and converting to linear polarization the polarization characteristic of the signal light after the signal light propagates through the object to be measured; frequency shifting means for shifting a frequency of the signal light and a frequency of the reference light relative to each other; superimposing means for superimposing the reference light and the signal light which is converted to linearly polarized light by the signal light polarizing means on each other to produce interference light, the frequency of the signal light and the frequency of the reference light being shifted relative to each other by the frequency shifting means; interference light separating means for separating a plurality of polarized light components which are different from each other from the produced interference light; one intensity modulating means for periodically modulating intensities of the polarized light components separated from the interference light based on a time difference corresponding to a phase difference of 180° in a beat of the interference light; one detecting means for receiving the polarized light components whose intensities are periodically modulated and outputting a detection signal including intensity change information of each of the polarized light components; and signal processing means for forming an image reflecting a birefringent property, of the object to be measured based on the intensity change information of each of the polarized light components included in the outputted detection signal.

According to a fourteenth aspect of the present invention, there is provided an optical image measuring apparatus according to the twelfth or thirteenth aspect of the invention, further including pulse signal generating means for generating a pulse signal having a frequency synchronized with frequency shift caused by the frequency shifting means, wherein the intensity modulating means periodically modulates the intensities of the polarized light components separated from the interference light based on the pulse signal generated by the pulse signal generating means.

According to a fifteenth aspect of the present invention, there is provided an optical image measuring apparatus according to the fourteenth aspect of the invention, in which the pulse signal generating means includes: a laser light source for emitting laser light; an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light; and auxiliary detection means for detecting the produced auxiliary interference light and outputting an electrical signal having a frequency substantially equal to a beat frequency of the auxiliary interference light, and wherein the pulse signal generating means generates the pulse signal having the frequency synchronized with the frequency of the electrical signal outputted from the auxiliary detection means.

According to a sixteenth aspect of the present invention, there is provided an optical image measuring method according to the fourteenth or fifteenth aspect of the invention, in which the intensity modulating means and the detecting means are provided for each of the plurality of polarized light components separated from the interference light, the pulse signal generating means outputs a plurality of pulse signals, each of which is the pulse signal, to the plurality of intensity modulation means, the optical image measuring apparatus further includes phase difference applying means for applying a phase difference among the plurality of pulse signals outputted from the pulse signal generating means and outputting the plurality of pulse signals among which the phase difference is applied, to the plurality of intensity modulation means, and the plurality of intensity modulation means modulates modulate the intensities of the plurality of the polarized light components using a time difference corresponding to the phase difference based on the pulse signals outputted from the phase difference applying means.

According to the first aspect of the present invention, there is provided an optical image measuring apparatus, including:

light beam outputting means for outputting a light beam whose intensity is periodically modulated;

beam diameter increasing means for increasing a beam diameter of the light beam;

linear polarization means for converting a polarization characteristic of the light beam to linear polarization;

light beam dividing means for dividing the light beam whose beam diameter is increased and polarization characteristic is converted to the linear polarization into signal light propagating to an object to be measured and reference light propagating to a reference object;

reference light polarizing means for converting a polarization characteristic of the reference light which is linearly polarized light;

signal light polarizing means for converting a polarization characteristic of the signal light which is linearly polarized light before the signal light propagates through the object to be measured and converting to linear polarization the polarization characteristic of the signal light after the signal light propagates through the object to be measured;

frequency shifting means for shifting a frequency of the signal light and a frequency of the reference light relative to each other;

superimposing means for superimposing the reference light whose polarization characteristic is converted by the reference light polarizing means and the signal light which is converted to linearly polarized light by the signal light polarizing means on each other to produce interference light, in which the frequency of the signal light and the frequency of the reference light are shifted relative to each other by the frequency shifting means;

interference light separating means for separating a plurality of polarized light components which are different from each other from the produced interference light;

detecting means for receiving the polarized light components separated from the interference light and outputting a detection signal including intensity change information of each of the polarized light components; and signal processing means for forming an image reflecting a birefringent property, of the object to be measured based on the intensity change information of each of the polarized light components included in the outputted detection signal. Therefore, even when the image reflecting the birefringent property, of the object to be measured is to be obtained over a wide range, a two-dimensional image of the object to be measured in a certain depth region can be obtained at a time, so that scanning with the signal light in an xy-plane direction is unnecessary unlike a conventional case. Thus, it is possible to effectively measure the image reflecting the birefringent property, of the object to be measured in a short time. Even when an image showing a three-dimensional birefringent distribution state of the object to be measured is to be obtained, it is only necessary to perform z-scanning using the reference object, so that the measurement can be effectively performed in a short time. Even when a one-dimensional birefringent distribution state is to be obtained, a part of the two-dimensional image obtained at a time may be used, so that efficient and effective image processing can be performed.

According to the twelfth aspect of the present invention, there is provided an optical image measuring apparatus, including:

a light source for continuously outputting a light beam;

beam diameter increasing means for increasing a beam diameter of the light beam;

linear polarization means for converting a polarization characteristic of the light beam to linear polarization;

light beam dividing means for dividing the light beam whose beam diameter is increased and polarization characteristic is converted to the linear polarization into signal light propagating to an object to be measured and reference light propagating to a reference object;

reference light polarizing means for converting a polarization characteristic of the reference light which is linearly polarized light;

signal light polarizing means for converting a polarization characteristic of the signal light which is linearly polarized light before the signal light propagates through the object to be measured and converting to linear polarization the polarization characteristic of the signal light after the signal light propagates through the object to be measured;

frequency shifting means for shifting a frequency of the signal light and a frequency of the reference light relative to each other;

superimposing means for superimposing the reference light whose polarization characteristic is converted by the reference light polarizing means and the signal light which is converted to linearly polarized light by the signal light polarizing means on each other to produce interference light, in which the frequency of the signal light and the frequency of the reference light are shifted relative to each other by the frequency shifting means;

interference light separating means for separating a plurality of polarized light components which are different from each other from the produced interference light;

intensity modulating means for periodically modulating intensities of the polarized light components separated from the interference light;

detecting means for receiving the polarized light components whose intensities are periodically modulated and outputting a detection signal including intensity change information of each of the polarized light components; and signal processing means for forming an image reflecting a birefringent property, of the object to be measured based on the intensity change information of each of the polarized light components included in the outputted detection signal. Therefore, even when the image reflecting the birefringent property, of the object to be measured is to be obtained over a wide range, a two-dimensional image of the object to be measured in a certain depth region can be obtained at a time, so that the measurement can be efficiently performed in a short time, as in the apparatus provided according to the first aspect.

According to the thirteenth aspect of the present invention, there is provided an optical image measuring apparatus, including:

a light source for continuously outputting a light beam;

beam diameter increasing means for increasing a beam diameter of the light beam;

linear polarization means for converting a polarization characteristic of the light beam to linear polarization;

light beam dividing means for dividing the light beam whose beam diameter is increased and polarization characteristic is converted to the linear polarization into signal light propagating to an object to be measured and reference light propagating to a reference object;

signal light polarizing means for converting a polarization characteristic of the signal light which is linearly polarized light before the signal light propagates through the object to be measured and converting to linear polarization the polarization characteristic of the signal light after the signal light propagates through the object to be measured;

frequency shifting means for shifting a frequency of the signal light and a frequency of the reference light relative to each other;

superimposing means for superimposing the reference light and the signal light which is converted to linearly polarized light by the signal light polarizing means on each other to produce interference light, in which the frequency of the signal light and the frequency of the reference light are shifted relative to each other by the frequency shifting means;

interference light separating means for separating a plurality of polarized light components which are different from each other from the produced interference light;

intensity modulating means for periodically modulating intensities of the plurality of polarized light components separated from the interference light based on a time difference corresponding to a phase difference of 180° in a beat of the interference light;

detecting means for receiving the polarized light components whose intensities are modulated and outputting a detection signal including intensity change information of each of the polarized light components; and signal processing means for forming an image reflecting a birefringent property, of the object to be measured based on the intensity change information of each of the polarized light components included in the outputted detection signal. Therefore, even when the image reflecting the birefringent property, of the object to be measured is to be obtained over a wide range, a two-dimensional image of the object to be measured in a certain depth region can be obtained at a time, so that the measurement can be efficiently performed in a short time, as in the apparatus provided according to the first or twelfth aspect.

BRIEF DESCRIPTION OF THE DRAWINGS

In the accompanying drawings:

FIGS. 2A to 2E are explanatory graphs showing interference light detection modes of the optical image measuring apparatus according to the first embodiment of the present invention, in which FIG. 2A illustrates a temporal waveform of a light beam whose intensity is modulated at a frequency and which is outputted from a broad-band light source, FIG. 2B illustrates a temporal waveform of an S-polarized light component of interference light in the case where the laser beam outputted from the broad-band light source is continuous light, FIG. 2C illustrates a temporal waveform of a P-polarized light component of the interference light in the case where the laser beam outputted from the broad-band light source is the continuous light, FIG. 2D illustrates a temporal waveform of the S-polarized light component of the interference light in the case where the intensity of the laser beam outputted from the broad-band light source is modulated, and FIG. 2E illustrates a temporal waveform of the P-polarized light component of the interference light in the case where the intensity of the laser beam outputted from the broad-band light source is modulated;

DETAILED DESCRIPTION OF THE PREFERRED EMBODIMENTS

An example of an optical image measuring apparatus according to each of preferred embodiments of the present invention will be described in detail with reference to the accompanying drawings.

First Embodiment

Structure of Apparatus

Figure 1:
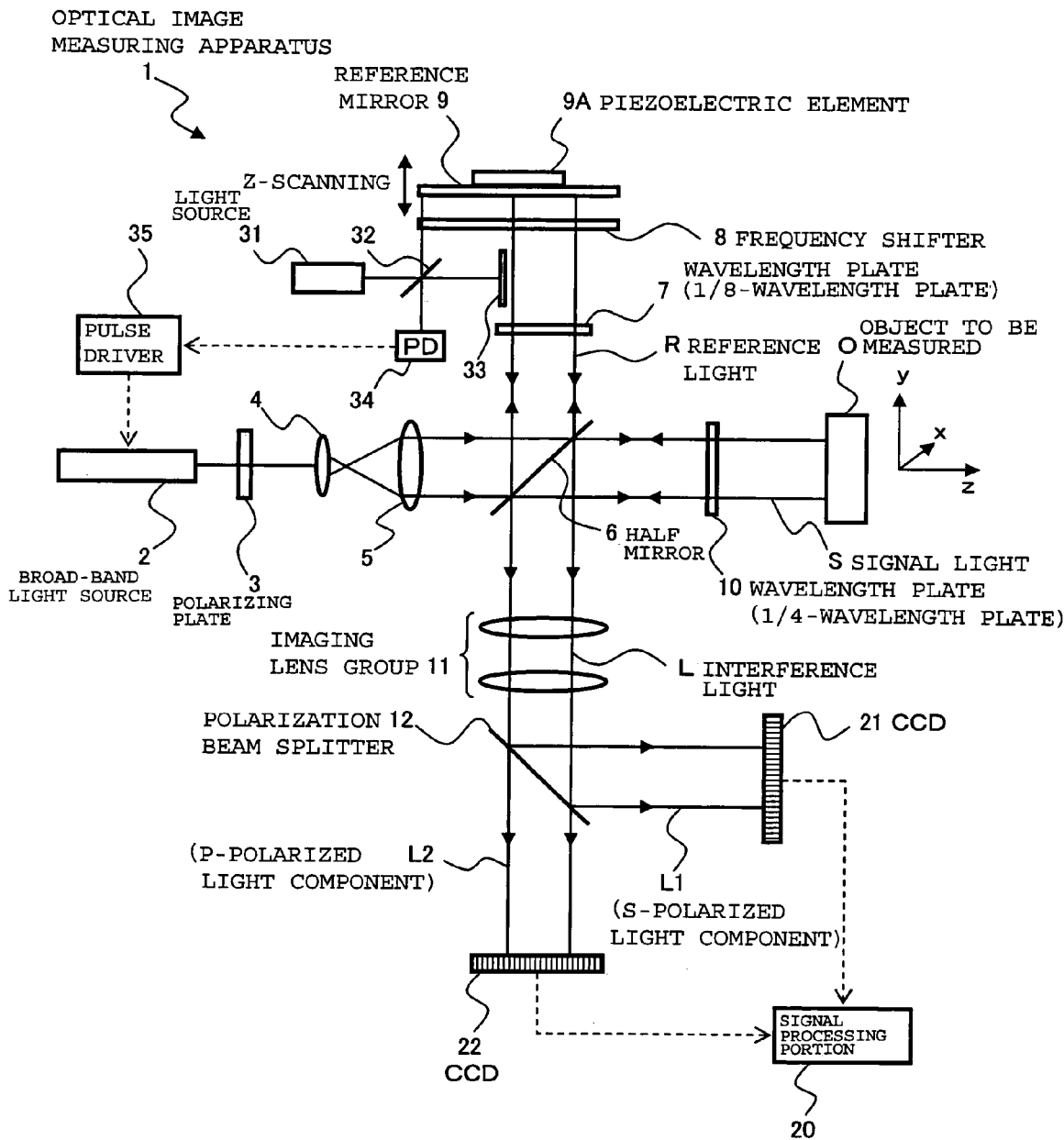
FIG. 1 is a schematic diagram showing an example of an optical image measuring apparatus according to a first embodiment of the present invention.

FIG. 1 is a schematic structural diagram showing an optical image measuring apparatus according to a first embodiment of the present invention. An optical image measuring apparatus 1 shown in FIG. 1 is an apparatus available to measure a tomographic image and a surface image of an object to be measured O which is made of a scattering medium in the medical field and the industrial field etc., in particular, to measure the tomographic image and the surface image of the object to be measured O which includes a layer having a birefringent property (birefringent layer), such as a retinal nerve fibre layer.

The optical image measuring apparatus 1 includes a broad-band light source 2 for outputting a low-coherent light beam, a polarizing plate 3 for converting a polarization characteristic of the light beam to linear polarization, lenses 4 and 5 for converting the light beam to a parallel light beam and increasing a beam diameter thereof, and a half mirror 6 for dividing the light beam into signal light S and reference light R and superimposing the signal light S and the reference light R on each other to produce interference light L. The optical image measuring apparatus 1 further includes a wavelength plate 7 for converting a polarization characteristic of the reference light R from linear polarization to circular polarization, a frequency shifter 8 for shifting a frequency of the reference light R, a reference mirror 9 for totally reflecting the reference light R on a reflective surface orthogonal to a propagating direction of the reference light R, a piezoelectric element 9A provided on a rear surface of the reference mirror 9 which is opposite to the reflective surface thereof and a wavelength plate 10 for converting a polarization characteristic of the signal light S.

The broad-band light source 2 corresponds to a "light source" in the present invention and is composed of an SLD, a light emitting diode (LED), or the like. Note that a coherent length of an available near-infrared region SLD is about 30 μm and a coherent length of a LED is about 10 μm. Further, the lenses 4 and 5 compose "beam diameter increasing means".

In an xyz-coordinate system shown in FIG. 1, a propagating direction of the light beam (in particular, the signal light S) outputted from the broad-band light source 2 is defined as a z-axis direction and an oscillation plane of the light beam orthogonal to the propagating direction thereof is defined as an xy-plane. The x-axis direction and a y-axis direction are defined so as to align with an oscillation plate of an electric field component of the light beam and an oscillation plate of a magnetic field component thereof, respectively. In other words, the z-axis direction corresponds to a depth direction of the object to be measured O. The x-axis direction corresponds to the horizontal direction, which is perpendicular to the z-axis direction. The y-axis direction corresponds to the vertical direction.

The polarizing plate 3 corresponds to the "first converting means" in the present invention and is a polarization conversion element for transmitting an oscillation component of the light beam in a predetermined direction, which is outputted from the broad-band light source 2. In this embodiment, the polarizing plate 3 is constructed to transmit an oscillation component in an angle direction by 45° with respect to an x-axis (and a y-axis) of the xy-plane. The light beam passing through the polarizing plate 3 has linearly polarized light by 45°. Therefore, the amplitudes of polarization components of the light beam in the x-axis direction and the y-axis direction are equal to each other. In other words, the amplitude of a P-polarized light component of the light beam is equal to that of a S-polarized light component thereof.

The half mirror 6 composes "light beam dividing means" in the present invention, for dividing the light beam of linear polarization which is converted to the parallel light beam into the signal light S propagating to the object to be measured O and the reference light R propagating to the reference mirror 9. The half mirror 6 reflects a part of the light beam as the reference light R and transmits the rest thereof as the signal light S.

The half mirror 6 composes the "superimposing means" in the present invention as well, which reflects a part of the signal light S propagating through the object to be measured O, and transmits a part of the reference light R propagating through the reference mirror 9, so that the signal light S and the reference light R are superimposed to produce the interference light L.

In this embodiment, because a Michelson interferometer is used, the dividing means and the superimposing means each are composed of (different reflective surface of) the same half mirror 6. On the other hand, when another type of interferometer such as a Mach-Zehnder interferometer is employed, an optical element composing the dividing means may be different from that composing the superimposing means. An arbitrary non-polarization beam splitter having no influence on the polarization characteristics of the light beams (signal light S and reference light R) is applied to each of the dividing means and the superimposing means.

The wavelength plate 7 composes "reference light polarizing means" in the present invention and is a polarization conversion element for converting the polarization characteristic of the reference light which is converted to linear polarization by the polarization plate 3. In this embodiment, a ⅛-wavelength plate is used as the wavelength plate 7. Therefore, when the reference light R passes through the wavelength plate 7, a phase difference of π/4 is provided between a P-polarized light component of the reference light R and an S-polarized light component thereof. In each of the case where the reference light R propagates from the half mirror 6 to the reference mirror 9 and the case where the reference light R is reflected on the reference mirror 9 and incident on the half mirror 6 again, the above-mentioned phase difference is applied to the reference light R. As a result, a phase difference of π/2 is applied to the reference light R. Thus, the wavelength plate 7 acts on the reference light R having linearly polarized light of 45° in the same manner as the ¼-wavelength plate, so the reference light R which is incident on the half mirror 6 again is converted to circularly polarized light. When another interferometer such as the Mach-Zehnder interferometer is used as described above, it is possible to apply the ¼-wavelength plate or the like as the reference light polarizing means.

The frequency shifter 8 composes the "frequency shifting means" in the present invention, imposing a frequency shift to the reference light R. The frequency shifter 8 is composed of, for example, an optoelectronic modulator or an acoustooptic modulator. As described later, it is possible to remove the frequency shifter 8 from the optical image measuring apparatus according to the present invention. In such a case, the frequency of the reference light R is shifted by moving the reference mirror 9.

The reference mirror 9 composes a "reference object" in the present invention and is moved in the optical path direction of the reference light R by the piezoelectric element 9A. Therefore, the reference mirror 9 acts to extract reflection light of the signal light S from the object to be measured O at each depth (z-coordinate) thereof. More specifically, because the light beam from the broad-band light source 2 is the low-coherent light, only the signal light S propagating a distance substantially equal to a propagating distance of the reference light R is useful to produce the interference light L. In other words, the signal light S reflected on a depth region of the object to be measured O which is located at a distance substantially equal to a distance to the reference mirror 9 relative to the half mirror 6 interferes with the reference light R to produce the interference light L. Therefore, the reference mirror 9 is moved in the optical path direction of the reference light R to change an optical path length of the reference light R. Thus, it is possible to change the depth of the object to be measured O in which the signal light S interfering with the reference light R is reflected. Such movement of the reference mirror 9 is called, for example, z-scanning.

The reference mirror 9 is vibrated by the piezoelectric element 9A in the optical path direction of the reference light R at a predetermined frequency with a predetermined amplitude. When the reference mirror 9 is to be vibrated, such vibration of the reference mirror 9 can be performed simultaneously with the z-scanning.

The piezoelectric element 9A can be used to continuously move the reference mirror 9 in the optical path direction of the reference light R to perform the z-scanning. When the reference mirror 9 is continuously moved, the reference light R is subjected to frequency shift at the time of reflection of the reference light R. Frequency shift applied by the movement of the reference mirror 9 may be referred to as Doppler frequency shift. The piezoelectric element 9A can be also used to move the reference mirror 9 stepwise at a predetermined step interval in a predetermined direction to perform the z-scanning.

The piezoelectric element 9A is controlled to vibrate in the optical path direction of the reference light R at a predetermined frequency with a predetermined amplitude. Therefore, the reference mirror 9 is vibrated in the optical path direction of the reference light R at the predetermined frequency with the predetermined amplitude. The control of the vibration frequency and the amplitude of the piezoelectric element 9A will be described later.

Although not shown, moving parameters (such as a moving speed, a moving distance, a moving time, a vibration frequency, and an amplitude) of the reference mirror 9 moved by the piezoelectric element 9A are controlled based on a mode of power supplied to the piezoelectric element 9A, such as a waveform of drive power supplied to the piezoelectric element 9A, as in a conventional case.

The reference mirror 9 and the piezoelectric element 9A compose "frequency shifting means" in the present invention based on the operating mode. Although described in a second embodiment, it is possible to employ a structure in which the reference mirror 9 and the piezoelectric element 9A are not used for frequency shift.

The wavelength plate 10 is disposed on the optical path of the signal light S. The wavelength plate 10 composes "signal light polarizing means" in the present invention and is a polarization conversion element for converting the polarization characteristic of the signal light S from linear polarization to circular polarization. A ¼-wavelength plate which acts to convert linearly polarized light of 45° to circularly polarized light and to convert circularly polarized light to linearly polarized light of 45° is used as the wavelength plate 10 in this embodiment. When the signal light S which is the light beam passing through the half mirror 6 passes through the wavelength plate 10, the signal light S is converted from the linearly polarized light to the circularly polarized light. Then, the signal light S which is the circularly polarized light is incident on the object to be measured O. When the signal light S propagating through the object to be measured O passes through the wavelength plate 10, the signal light S is converted from the circularly polarized light to the linearly polarized light and guided to the half mirror 6.

The optical image measuring apparatus 1 according to this embodiment further includes an imaging lens group 11 for imaging the interference light L produced by the half mirror 6 serving as the superimposing means, a polarization beam splitter 12 for separating a plurality of components having different polarization characteristics (polarized light components) from the interference light L passing through the imaging lens group 11, CCDs (cameras) 21 and 22 provided on optical paths of the separated polarized light components, and a signal processing portion 20 for processing results obtained by detection with the CCDs 21 and 22.

The polarization beam splitter 12 composes "interference light separating means" in the present invention and acts to separate the plurality of different polarized light components from the interference light L. More specifically, the polarization beam splitter 12 acts to reflect the S-polarized light component L1 of the interference light L to allow the reflected S-polarized light component L1 to enter the CCD 21 and to transmit the P-polarized light component L2 thereof to allow the transmitted P-polarized light component L2 to enter the CCD 22. The amplitude (that is, maximum intensity) of the S-polarized light component L1 of the interference light L is equal to that of the P-polarized light component L2 thereof.

The CCDs 21 and 22 compose "detecting means" in the present invention and each are a storage type two-dimensional photo sensor array for interference light detection. The CCD 21 receives the S-polarized light component L1 of the interference light L which is reflected on the polarization beam splitter 12 and performs its photoelectric conversion, thereby generating a detection signal including information on a change in intensity of the S-polarized light component L1 and outputting the detection signal to the signal processing portion 20. Similarly, the CCD 22 receives the P-polarized light component L2 of the interference light L which passes through the polarization beam splitter 12 and performs its photoelectric conversion, thereby generating a detection signal including information on a change in intensity of the P-polarized light component L2, and outputting the detection signal to the signal processing portion 20. Each of the detection signals outputted from the CCDs 21 and 22 to the signal processing portion 20 is the above-mentioned heterodyne signal.

The signal processing portion 20 executes calculation processing described later based on the detection signals outputted from the CCDs 21 and 22. The signal processing portion 20 analyzes a result obtained by the calculation processing to form various images including a tomographic image of the object to be measured O and causes a display device such as a monitor device (not shown) to display the formed images. Although described in detail later, when the object to be measured O includes the birefringent layer, the signal processing portion 20 forms an image reflecting a birefringent property, of the object to be measured O. In order to perform such processing, the signal processing portion 20 is composed of, for example, a computer which includes: a storage device storing a predetermined calculation program, such as a ROM; and a calculation control device executing the calculation program, such as a CPU. The signal processing portion 20 is "signal processing means" in the present invention.

The optical image measuring apparatus 1 according to this embodiment further includes a light source 31, a beam splitter 32, a reflecting mirror 33, a photo detector (PD) 34, and a pulse driver 35 in order to modulate the amplitude of the light beam from the broad-band light source 2 while frequency shift applied to the reference light R is monitored.

The laser light source 31 is composed of a laser diode for emitting laser light having a coherent length longer than that of the light beam from the broad-band light source 2. The beam splitter 32 divides the laser light from the laser light source 31 into first laser light (reflection light) propagating through the frequency shifter 8 and the reference mirror 9 and second laser light (transmission light) propagating through the reflecting mirror (fixed mirror) 33 disposed to be fixed. Then, the beam splitter 32 superimposes the first laser light which has been subjected to frequency shift by the frequency shifter 8 or the like and the second laser light reflected on the reflecting mirror 33 on each other to produce interference light. The interference light produced different from the interference light L is to be called "auxiliary interference light". The beam splitter 32, the reflecting mirror 33, and the reference mirror 9 compose an "auxiliary interference light" in the present invention.

The photo detector 34 composes "auxiliary detecting means" in the present invention. The photodetector 34 detects the auxiliary interference light produced by the auxiliary optical interference system and outputs an electrical signal having a frequency equal to beat signal of the auxiliary interference light. The pulse driver 35 composes "light source generating means" in the present invention. The pulse driver 35 generates a pulse signal having a frequency equal to that of the electrical signal outputted from the photo detector 34 and outputs the pulse signal to the broad-band light source 2.

The broad-band light source 2 is driven based on the pulse signal outputted from the pulse driver 35 to output a pulsed light beam having a frequency equal to that of the pulse signal. The pulse signal from the pulse driver 35 is set to, for example, an electrical signal of a rectangular train with a duty of 50%. At this time, the broad-band light source 2 outputs the pulsed light beam of a rectangular train with a duty of 50%. A duty ratio of the light beam outputted from the broad-band light source 2 is not limited to 50% and thus an arbitrary duty ratio can be applied. The pulse driver 35 generates a pulse signal for obtaining the duty ratio of the light beam. The duty ratio can be set and changed by, for example, the computer composing the signal processing portion 20.

The broad-band light source 2, the laser light source 31, the beam splitter 32, the reflecting mirror 33, the photo detector (PD) 34, and the pulse driver 35 compose "light beam outputting means" in the present invention. The laser light source 31, the beam splitter 32, the reflecting mirror 33, the photo detector (PD) 34, and the pulse driver 35 compose "pulse generating means" in the present invention.

The vibration frequency of the piezoelectric element 9A for vibrating the reference mirror 9 to perform the measurement is set to a frequency synchronized with that of the electrical signal outputted from the photo detector 34 (for example, a frequency equal to that of the electrical signal). The amplitude of vibration of the reference mirror 9 is set to an amplitude corresponding to, for example, ½ of the wavelength of the electrical signal from the photodetector 34 (amplitude can be arbitrarily set). Therefore, for example, it is possible to provide a circuit operative to generate an electrical signal (drive signal) having the vibration frequency and an amplitude for vibrating the reference mirror 9 by the amplitude based on the electrical signal from the photo detector 34 and output the generated electrical signal to the piezoelectric element 9A. Assume that a relationship between the amplitude of the drive signal sent to the piezoelectric element 9A and the actual amplitude of vibration of the piezoelectric element 9A is known. For example, the circuit sets the amplitude of the drive signal based on the relationship.

Measurement Mode

Subsequently, a measurement mode on the spatial signal intensity distribution of the interference light L and the spatial phase distribution thereof, that is, a measurement mode on the heterodyne signal intensity, which is executed by the optical image measuring apparatus 1 according to this embodiment will be described. The computation processing and image forming processing described below in detail is executed by the signal processing portion 20.

First, the basic principle of measurement executed by the optical image measuring apparatus 1 will be described. The light beam outputted from the broad-band light source 2 is converted to the linearly polarized light in the angle direction of 45° relative to each of the x-axis and the Y-axis by the polarizing plate 3. The beam diameter of the converted linearly polarized light is increased by the lenses 4 and 5 and the linearly polarized light whose beam diameter is increased is converted to the parallel light beam thereby. Then, the light beam is incident on the half mirror 6 and divided into two, that is, the signal light S and the reference light R. The signal light S and the reference light R each have a linear polarized light of 45°.

The signal light S is converted from the linearly polarized light to the circularly polarized light by the wavelength plate 10. Then, the signal light S is incident on the object to be measured O and reflected on a surface thereof and various depth regions thereof. When the signal light S reflected on or in the object to be measured O passes through the wavelength plate 10 again, the signal light S is converted from the circularly polarized light to the linearly polarized light of 45°. The signal light S of the linearly polarized light is incident on the half mirror 6 again and a part thereof is reflected on the half mirror 6. Even when the signal light S propagating through the object to be measured O has a phase difference, the signal light S is converted to the linearly polarized light of 45° by the wavelength plate 10 and a ratio between the S-polarized light component L1 of the interference light L and the P-polarized light component L2 thereof is constantly maintained to a predetermined ratio. Therefore, the measurement can be efficiently performed.

On the other hand, the reference light R passes through the wavelength plate 7 and the frequency shifter 8 and propagates to the reference mirror 9. At this time, assume that the reference mirror 9 is moving (that is, z-scanning and/or vibration are performing) in the optical path direction of the reference light R by the piezoelectric element 9A. The reference light R is subjected to frequency shift having a predetermined amount using the frequency shifter 8 and frequency shift based on the movement of the reference mirror 9. Because the polarization characteristic of the reference light R is the linearly polarized light of 45° and the wavelength plate 7 is the ⅛-wavelength plate, the reference light R passing through the wavelength plate 7 two times is converted to the circularly polarized light. Then, the reference light R of the circularly polarized light is incident on the half mirror 6 again. The half mirror 6 transmits a part of the reference light R.

When the signal light S of the linearly polarized light of 45° which propagates through the object to be measured O and the reference light R which is subjected to frequency shift and converted to the circularly polarized light pass through the half mirror 6, the signal light S and the reference light R are superimposed on each other to produce the interference light L. The interference light L has a beat frequency corresponding to the amount of frequency shift applied to the reference light R. The interference light L produced by the half mirror 6 propagates the polarization beam splitter 12 through the imaging lens group 11.

The polarization beam splitter 11 acts to reflect the S-polarized light component L1 of the interference light L and to transmit the P-polarized light component L2 thereof. The S-polarized light component L1 of the interference light L is detected by the CCD 21 and the P-polarized light component L2 thereof is detected by the CCD 22. The S-polarized light component L1 of the interference light L includes an S-polarized light component Ess of the signal light S and an S-polarized light component Ers of the reference light R. The P-polarized light component L2 of the interference light L includes a P-polarized light component Esp of the signal light S and a P-polarized light component Erp of the reference light R. The S-polarized light component Ess of the signal light S, the P-polarized light component Esp thereof, the S-polarized light component Ers of the reference light R, and the P-polarized light component Erp thereof each are expressed by the following expressions.

$$Ess = \sqrt{I_{ss}} \sin(2\pi f t + \phi) \quad (2)$$

$$Esp = \sqrt{I_{sp}} \sin(2\pi f t + \phi) \quad (3)$$

$$Ers = \sqrt{I_{rs}} \sin[2\pi(f+f_D)t + \phi'] \quad (4)$$

$$Erp = \sqrt{I_{rp}} \sin[2\pi(f+f_d)t + \phi' + 90°] \quad (5)$$

Here, f indicates a frequency of the light beam emitted from the broad-band light source 2, $f_D$ indicates a frequency shift, $\phi$ indicates an initial phase of the signal light S, and $\phi'$ indicates an initial phase of the reference light R. Assume that a difference between the initial phase of the signal light S and the initial phase of the reference light R is given by $\Delta\phi(=\phi-\phi')$. Referring to the expressions (2) to (5), the S-polarized light component L1 of the interference light L and the P-polarized light component L2 thereof are detected by the CCDs 21 and 22 as heterodyne signals $i_1$ and $i_2$ expressed by the following expressions.

$$i_1 \propto |E_{ss}+E_{rs}|^2 \propto I_{rs}+I_{ss}+2\sqrt{I_{rs}I_{ss}} \cos(2\pi f_D t + \Delta\phi) \quad (6)$$

$$i_2 \propto |E_{sp}+E_{rp}|^2 \propto I_{rp}+I_{sp}+2\sqrt{I_{rp}I_{sp}} \sin(2\pi f_D t + \Delta\phi) \quad (7)$$

As is apparent from the comparison between the expressions (6) and (7), a phase difference between the alternating signals of the third terms of the respective expressions is 90° because of the cosine and sine functions with the same phase. The optical image measuring apparatus 1 according to this embodiment performs the following measurement utilizing such a feature.

As described above, in the optical image measuring apparatus 1, the broad-band light source 2 is controlled using the laser light source 31, the beam splitter 32, the reflecting mirror 33, the photo detector (PD) 34, and the pulse driver 35.

The laser light outputted from the light source 31 is divided into an optical path in the reference mirror 9 direction (reflection laser light beam) and an optical path in the fixed mirror 33 direction (transmission laser light beam) by the beam splitter 32. The laser light beam on the optical path in the reference mirror 9 direction propagates through the frequency shifter 8 and the reference mirror 9 to be subjected to frequency shift by those and then is incident on the beam splitter 32 again. On the other hand, the laser light beam on the optical path in the fixed mirror 33 direction is incident, as reflection light on the fixed mirror 33, on the beam splitter 32 again (without frequency shift). The laser light beams propagating on both the optical paths are superimposed on each other by the beam splitter 33 to produce interference light. The interference light is detected by the photo detector 34.

As in the case of the reference light R, the auxiliary interference light is subjected to the frequency shift using the frequency shifter 8 and the frequency shift using the reference mirror 9. Therefore, the auxiliary interference light is subjected to frequency shift having the amount of shift (substantially) equal to that applied to the reference light R. Thus, the auxiliary interference light has a beat frequency (substantially) equal to that of the interference light L produced from the signal light S and the reference light R.

The photo detector 34 outputs an electrical signal corresponding to the detected auxiliary interference light to the pulse driver 35. As in the case of the heterodyne signal expressed by the expression (1), the electrical signal includes a direct current component and an alternating current component. The alternating current component has a frequency substantially equal to the beat frequency of the interference light L as described above. When receiving the electrical signal from the photo detector 34, the pulse driver 35 outputs a pulse signal having a frequency equal to that of the electrical signal to the broad-band light source 2. The broad-band light source 2 is driven based on the pulse signal outputted from the pulse driver 35 and outputs a pulsed light beam having a repetition frequency equal to that of the pulse signal.

Therefore, in the optical image measuring apparatus 1, the amount of frequency shift applied to the reference light R is monitored and the object to be measured O is measured using a pulsed light beam having a frequency synchronized with (for example, substantially equal to) the amount of frequency shift. As described above, the light beam from the broad-band light source 2 is outputted as, for example, pulsed light of a rectangular train with a duty of 50%.

The duty ratio of the light beam outputted from the broad-band light source 2 is not limited to 50%. The pulse shape of the light beam may be a train other than the rectangular train (for example, a triangular train or a trapezoidal train). For example, a light beam obtained by modulation between output intensities of 50 and 100 can be also applied instead of pulsed light obtained by switching between output intensities of 0 and 100. In this case, it is possible to employ, for example, a structure for modulating the output light intensity of the broad-band light source 2 or a structure for inserting and removing a filter to and from the optical path of the light beam to modulate the intensity of the light beam. That is, the important point is not to control the modulation degree of the intensity of the light beam but to control a frequency for modulation of the intensity thereof so that the frequency is synchronized with the beat frequency of the interference light L (modulation frequency becomes substantially equal to the beat frequency).

Next, a detection mode of the interference light L in the optical image measuring apparatus 1 according to this embodiment will be described with reference to graphs shown in FIGS. 2A to 2E. Hereinafter, assume that a modulation frequency of the intensity of the light beam outputted from the broad-band light source 2 is $f_m$. As described above, $f_D$ indicates the frequency shift applied to the reference light R (beat frequency of the interference light L). Assume that the modulation frequency $f_m$ of the light beam is equal to or closer to the frequency shift $f_D$.

Figure 2:
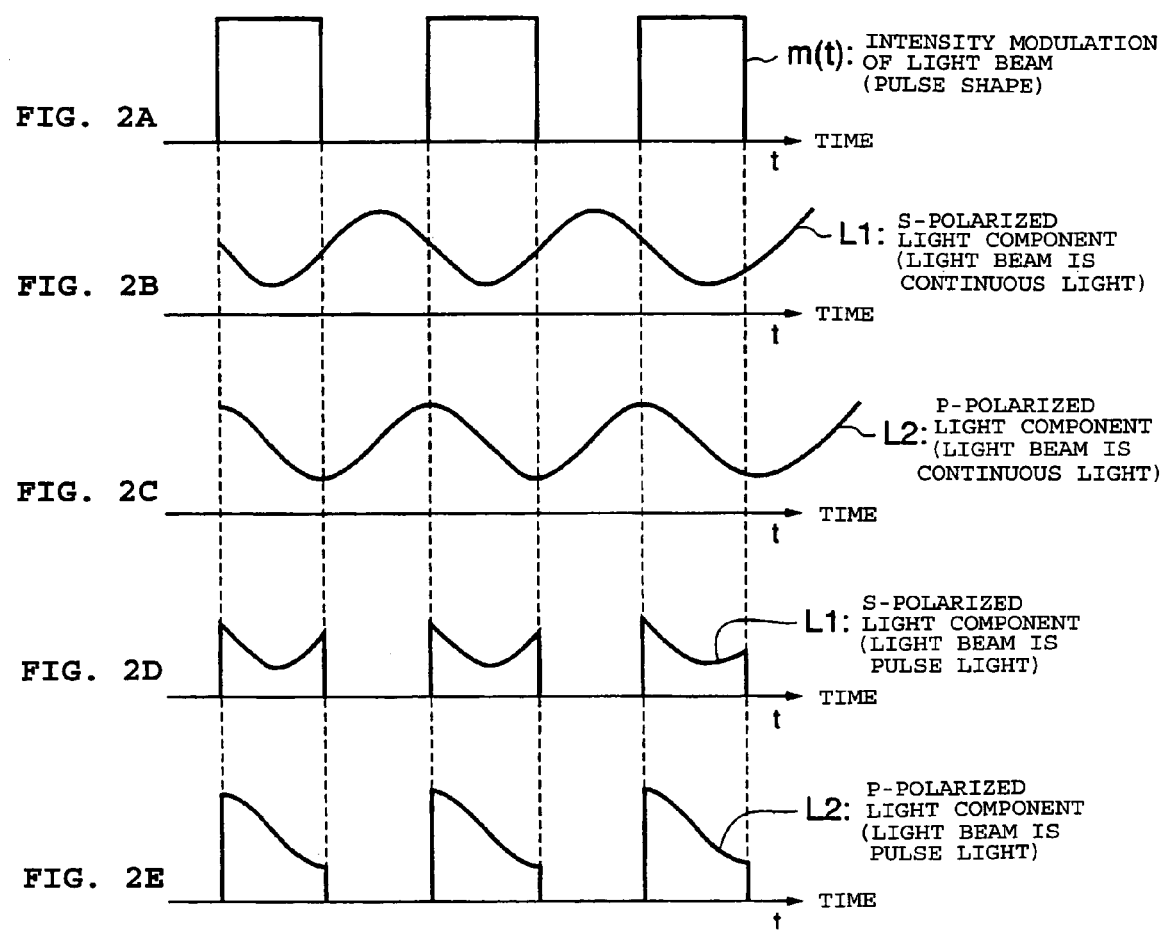

FIG. 2A shows a temporal waveform of a light beam which is subjected to intensity modulation at the modulation frequency $f_m$ and outputted from the broad-band light source 2. FIG. 2B shows a temporal waveform of the S-polarized light component L1 of the interference light L (beat frequency $f_D$) in the case where the light beam is continuous light and thus the reference light R and the signal light S each are continuous light. FIG. 2C shows a temporal waveform of the P-polarized light component L2 of the interference light L in the case where the reference light R and the signal light S each are continuous light. Note that a phase difference between the S-polarized light component L1 and the P-polarized light component L2 as shown in FIGS. 2B and 2C is 90°.

FIG. 2D shows a temporal waveform of the S-polarized light component L1 of the interference light L in the case where the light beam from the broad-band light source 2 is subjected to the intensity modulation as shown in FIG. 2A (this corresponds to FIG. 2B). FIG. 2E shows a temporal waveform of the P-polarized light component L2 of the interference light L in the case where the light beam from the broad-band light source 2 is subjected to the intensity modulation as shown in FIG. 2A (this corresponds to FIG. 2C). A phase difference between the S-polarized light component L1 and the P-polarized light component L2 as shown in FIGS. 2D and 2E is 90°.

The CCD 21 detects the S-polarized light component L1 having the temporal waveform shown in FIG. 2D. The light beam from the broad-band light source 2 is a light pulse of a rectangular train having the frequency $f_m$ and a duty of 50%. When a difference between the modulation frequency $f_m$ and the beat frequency $f_D$ of the interference light L ($\delta f = |f_m - f_D|$) is sufficiently smaller than a response frequency of the CCD 21 serving as the storage type photo sensor, a detection signal of the S-polarized light component L1 which is outputted from the CCD 21 becomes proportional to the amount of photo charge stored for a detection period. Therefore, the detection signal is expressed by the following expression (for example, see M. Akiba, K. P. Chan, and N. Tanno, Japanese Journal of Applied Physics, Vol. 39, L1194 (2000)).

$$S_1 = \langle K_1 m(t) i_1(t) \rangle \tag{8}$$
$$= K_1 \left[ \frac{1}{2} I_{ss} + \frac{1}{2} I_{rs} + \frac{2}{\pi} \sqrt{I_{ss} I_{rs}} \cos\Psi \right]$$

Here, <•> indicates a time average produced by a storage effect of the CCD 21. In addition, $K_1$ indicates photo detection efficiency including reflectance of the polarization beam splitter 11 and a photoelectric conversion rate of the CCD 21, m(t) indicates a function for modulating the output intensity of the broad-band light source 2 (function indicating a rectangular pulse), and ψ indicates an initial phase value for measurement.

As is apparent from the expression (8), the detection signal outputted from the CCD 21 includes the 3rd term related to an amplitude $\sqrt{(I_{ss} I_{rs})}$ of the S-polarized light component L1 of the interference light L and an early phase (ψ) thereof in addition to the terms related to the intensity of the signal light S and the term related to the intensity of the reference light R (first and second terms and background light component).

Similarly, the CCD 22 detects the P-polarized light component L2 having the temporal waveform shown in FIG. 2E and outputs a detection signal as expressed by the following expression.

$$S_2 = K_2 \left[ \frac{1}{2} I_{sp} + \frac{1}{2} I_{rp} + \frac{2}{\pi} \sqrt{I_{sp} I_{rp}} \sin\Psi \right] \tag{9}$$

Here, $K_2$ indicates photo detection efficiency including transmittance of the polarization beam splitter 11 and a photoelectric conversion rate of the CCD 22.

Next, calculation processing of the signal intensity of the interference light L based on the detection signals (expressed by the expressions (8) and (9)) outputted from the CCDs 21 and 22 will be described.

The first term and the second term of the right side of each of the expressions (8) and (9) indicate the intensity of the background light. The intensity of the background light may be measured in advance or separately. For example, a light beam which is continuous light is outputted from the broadband light source 2 and detected by the CCD 21 and the like. The detected light beam is integrated for a period corresponding to, for example, one wavelength (or integral multiple thereof). Therefore, the third term (alternating component; phase quadrature component) of each of the expressions (8) and (9) is cancelled to obtain the intensity of the background light (background light component). A part of the interference light L may be separated therefrom by the beam splitter and detected by the CCD to obtain the intensity of the background light.

The obtained intensity of the background light component of the interference light L is subtracted from each of the intensities of the detection signals of the S-polarized light component L1 and the P-polarized light component L2 expressed by the expressions (8) and (9) to calculate phase quadrature components (alternating components) of the respective detection signals, that is, a phase quadrature component $S_1'$ of the S-polarized light component L1 of the interference light L and a phase quadrature component $S_2'$ of the P-polarized light component L2 thereof (see the following expressions).

$$S_1' = K_1 \frac{2}{\pi} \sqrt{I_{ss} I_{rs}} \cos\Psi \qquad (10)$$

$$S_2' = K_2 \frac{2}{\pi} \sqrt{I_{ss} I_{rs}} \sin\Psi \qquad (11)$$

Because the object to be measured O has a birefringent property as in the case of the retinal nerve fibre layer of an eye, the object to be measured O may act as a phase retarder as expressed by the following expression (operator for delaying a phase) on the two quadrature polarized component of the signal light S.

$$S(\alpha, \beta) = \begin{vmatrix} \cos^2\beta + \sin^2\beta e^{-j2\alpha} & \cos\beta\sin\beta(1 - e^{-j2\alpha}) \\ \cos\beta\sin\beta(1 - e^{-j2\alpha}) & \cos^2\beta e^{-j2\alpha} + \sin^2\beta \end{vmatrix} \qquad (12)$$

Here, $\alpha$ denotes an average value of phase advance and delay between incident light of the signal light S which is incident on the object to be measured O and reflection light thereof which is reflected thereon. In addition, $\beta$ denotes an average tilt angle of a fast axis (axis in which the propagation velocity of light is fast) in the birefringent layer of the object to be measured O.

Therefore, the phase quadrature component $S_1'$ of the S-polarized light component L1 of the interference light L and the phase quadrature component $S_2'$ of the P-polarized light component L2 thereof as expressed by the expressions (10) and (11) are re-expressed by the following expressions.

$$S_1'' = K_1 \frac{2}{\pi} \sqrt{I_{ss} I_{rs}} \cos(\Psi + \alpha) \qquad (13)$$

$$S_2'' = K_2 \frac{2}{\pi} \sqrt{I_{ss} I_{rs}} \sin(\Psi + \alpha) \qquad (14)$$

Because the reference light R is converted to the circularly polarized light by the wavelength plate 7, an intensity $I_{rs}$ of an S-polarized light component Ers of the reference light R may be substantially equal to an intensity $I_{rp}$ of a P-polarized light component Erp thereof (this indicates $I_{rs} \approx I_{rp} = I_r$). It can be considered that the reflection light of the signal light S on the object to be measured O does not significantly depends on the polarization characteristic of the incident light thereof, so an intensity $I_{ss}$ of an S-polarized light component Ess of the signal light S may be substantially equal to or close to an intensity $I_{sp}$ of a P-polarized light component Esp thereof (this indicates $I_{ss} \approx I_{sp} = I_s$). Because the signal light S is scattered or absorbed in the object to be measured O, it can be assumed that the intensity of the signal light S included in the interference light L is normally sufficiently smaller than that of the reference light R included in the interference light L ($I_s << I_r$). Thus, the following relationship is obtained based on the expressions (13) and (14).

$$\alpha = \tan^{-1}\left(\frac{K_1 S_2''}{K_2 S_1''}\right) - \Psi \qquad (15)$$

The expression (15) indicates $\alpha$ (average value of phase advance and delay) which is a parameter related to the birefringent property of the object to be measured O.

When a tomographic image of the object to be measured O at a certain depth ($z_0$=constant), that is, an xy-plane image is to be formed, $\alpha$-values $\alpha(x, y, z_0)$ at coordinates (x, y, $z_0$) on a plane $z=z_0$ are compared with one another and a distribution state of the $\alpha$-values on the plane is expressed based on a display contrast, a display color, and the like. Therefore, a birefringent distribution state of the object to be measured O at the depth $z_0$ can be effectively imaged.

The same holds for the case where a tomographic image of the object to be measured O in the depth direction thereof is to be formed. For example, when a tomographic image ($x_0$=constant), that is, a yz-plane image is to be formed, $\alpha$-values $\alpha(x_0, y, z)$ at coordinates ($x_0$, y, z) on a plane $x=x_0$ are compared with one another and a distribution state of the $\alpha$-values on the plane is expressed based on a display contrast, a display color, and the like. Therefore, a birefringent distribution of the object to be measured O along a cross section ($x_0$=x) in the depth direction can be effectively imaged. The same holds for the case where a tomographic image ($y_0$=constant) is to be formed.

According to the optical image measuring apparatus 1, it is also possible to form not only the two-dimensional tomographic image but also an image expressing a one-dimensional or three-dimensional birefringent distribution state. For example, $\alpha$-values $\alpha(x, y, z)$ at arbitrary coordinates (x, y, z) of the object to be measured O are obtained and the obtained $\alpha$-values $\alpha(x, y, z)$ are combined with one another based on the arbitrary coordinates (x, y, z) for image formation. It is possible to form a two-dimensional image along an arbitrary cross section (including an oblique cross section) of the object to be measured O.

On the other hand, when the expressions (13) and (14) are used, a combination between amplitude of the S-polarized light component L1 of the interference light L and an amplitude of the P-polarized light component L2 thereof, that is, an intensity distribution of the interference light L is expressed by the following expression.

$$\sqrt{I_s I_r} \propto \sqrt{S_1''^2 + S_2''^2} \qquad (16)$$

Effect

As described above, according to the optical image measuring apparatus 1, even when the image reflecting the birefringent property, of the object to be measured O is to be obtained over a wide range, the two-dimensional image (image on the xy-plane) of the object to be measured O in a certain depth region can be obtained at a time. Therefore, scanning with the signal light S in the xy-direction is unnecessary unlike a conventional case. Thus, the image reflecting the birefringent property, of the object to be measured O can be effectively measured in a short time. Even when an image showing a three-dimensional birefringent distribution state of the object to be measured O is to be obtained, it is only necessary that the z-scanning using the reference mirror 9 be performed to scan the object to be measured O in the depth direction (z-direction). Therefore, similarly, the measurement can be effectively performed in a short time. Even when a one-dimensional birefringent distribution state is desired, efficient and effective image processing can be performed using a part of a two-dimensionally obtained distribution.

MODIFIED EXAMPLE

In the above-mentioned structure, the light beam from the broad-band light source 2 is converted to the linearly polarized light and then divided into the signal light S and the reference light R. Each of the signal light S and the reference light R may be converted to the linearly polarized light after the division of the light beam. In such a case, it is necessary to provide a polarizing plate on each of the optical path of the signal light S and the optical path of the reference light R, so the optical image measuring apparatus becomes slightly more complex than the above-mentioned structure. Therefore, the above-mentioned structure may be more suitable in practical use.

Further in the above-mentioned embodiment, a light source 31 for monitoring the shift amount of the frequency of the reference light R, the beam splitter 32, the reflection mirror 33 and the photo detector 34 are provided, and its monitoring result is adapted to feedback to the intensity modulation of the light beam, but for instance when the frequency shift amount for investing the reference light R is set, by providing a light source driving device for forming voluntarily a pulse signal of the frequency synchronized thereto may control the intensity modulation of the light beam.

In the above-mentioned embodiment, the measurement mode for obtaining the tomographic image of the object to be measured O at each depth during the z-scanning using the reference mirror 9 is described. When the measurement is performed while the position of the reference mirror 9 is fixed, it is possible to obtain a still image and a dynamic picture image of the object to be measured O at a certain depth with high precision.

The detecting means of the optical image measuring apparatus 1 are not limited to the above-mentioned CCDs. It is only necessary that the detecting means have both a function of detecting the interference light and performing photoelectric conversion thereon and a function of storing detected charges.

The optical image measuring apparatus 1 having the Michelson type interferometer is described. It is also possible to use an arbitrary interferometer such as a Mach-Zehnder type interferometer or a Fizeau interferometer (for example, see JP 3245135 B made by the inventors of the present invention).

An optical fiber (bundle) used as a light guide member is provided in a part of the interferometer. Therefore, the degree of freedom of an apparatus design can be improved, the apparatus can be made compact, or the degree of freedom of location of the object to be measured can be improved (for example, see JP 3245135 B).

A structure for periodically cutting off a continuous light beam (continuous light) at a frequency synchronized with the beat frequency of the interference light L instead of the structure for pulse-driving the broad-band light source 2 can be used to periodically modulate the intensity of the light beam.

Figure 3:
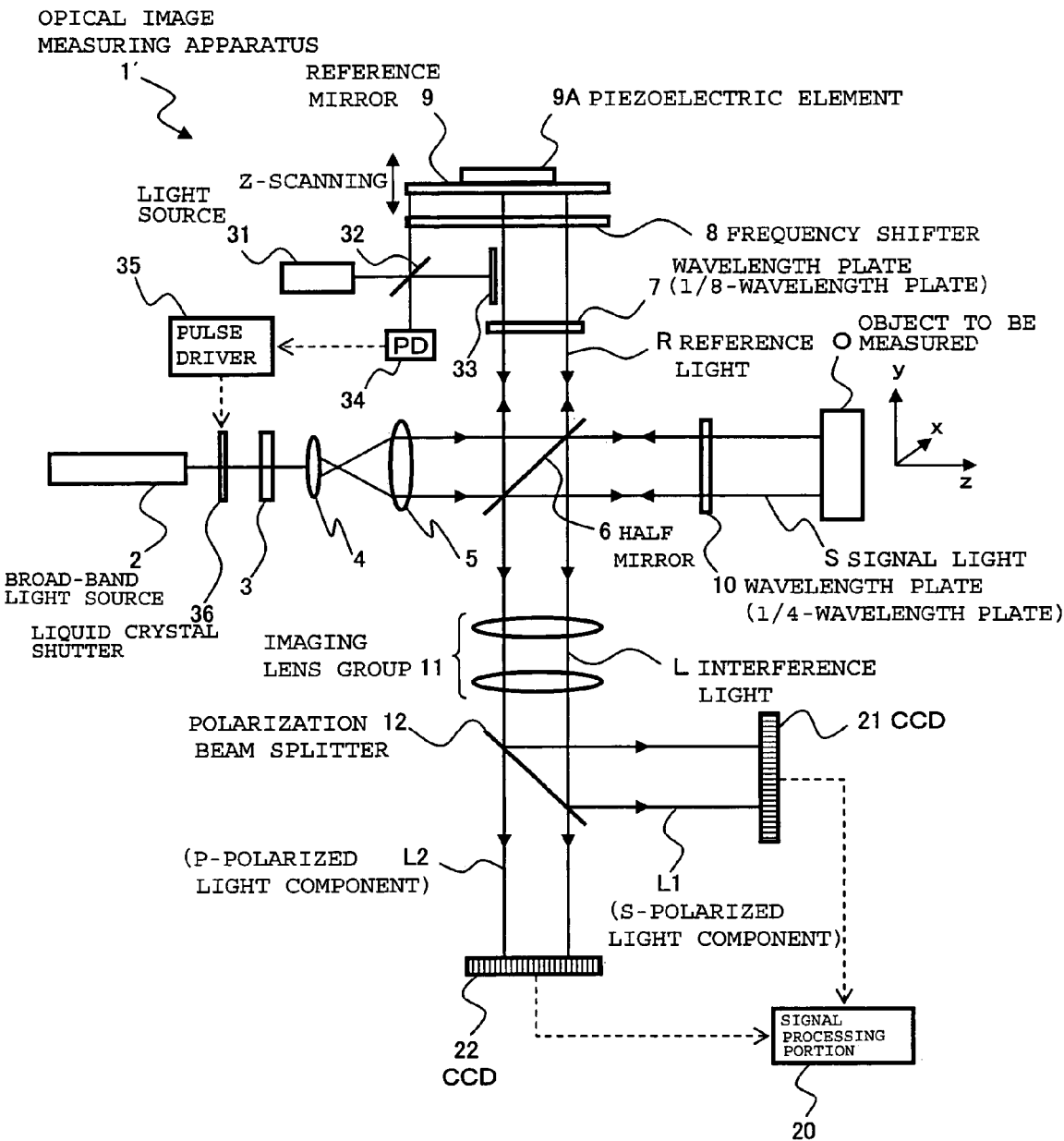
FIG. 3 is a schematic diagram showing a modified example of the optical image measuring apparatus according to the first embodiment of the present invention.

FIG. 3 illustrates an example of an optical image measuring apparatus having the above-mentioned structure. An optical image measuring apparatus 1' shown in FIG. 3 includes a liquid crystal shutter 36 provided between the broad-band light source 2 for outputting the continuous light beam and the polarizing plate 3. The liquid crystal shutter 36 composes "shutter means" in the present invention and periodically cuts off the light beam in response to the pulse signal generated by the pulse driver 35 as in the above-mentioned embodiment.

The pulse driver 35 receives an electrical signal (having a frequency substantially equal to the beat frequency of the interference light L) outputted from the photodetector 34, generates a pulse signal having a frequency synchronized with (for example, a frequency two times) the frequency of the received electrical signal, and outputs the generated pulse signal to the liquid crystal shutter 36.

The liquid crystal shutter 36 is opened and closed in response to the pulse signal outputted from the pulse driver 35. For example, the shutter is opened in response to a first pulse to transmit the light beam. Next, the shutter is closed in response to a second pulse to cut off the light beam. Then, the shutter is opened in response to a third pulse to transmit the light beam. The shutter is closed in response to a fourth pulse to cut off the light beam. Such shutter opening and closing operations are periodically repeated. Therefore, the continuous light beam outputted from the broad-band light source 2 is incident on the polarizing plate 3 at the frequency substantially equal to the beat frequency of the interference light L. Thus, the image of the object to be measured O can be obtained as in the above-mentioned embodiment.

In this modified example, the pulse driver 35 composes "shutter driving means" in the present invention. The broad-band light source 2 composes a "light source" in the present invention. The broad-band light source 2, the laser light source 31, the beam splitter 32, the reflecting mirror 33, the photo detector 34, the pulse driver 35, and the liquid crystal shutter 36 compose "light beam outputting means" in the present invention.

Second Embodiment

Subsequently, an optical image measuring apparatus according to a second embodiment of the present invention will be described. In this embodiment, interference light beams produced based on a continuously outputted light beam instead of the light beam whose intensity is modulated as in the first embodiment are sampled using shutters.

Figure 4:
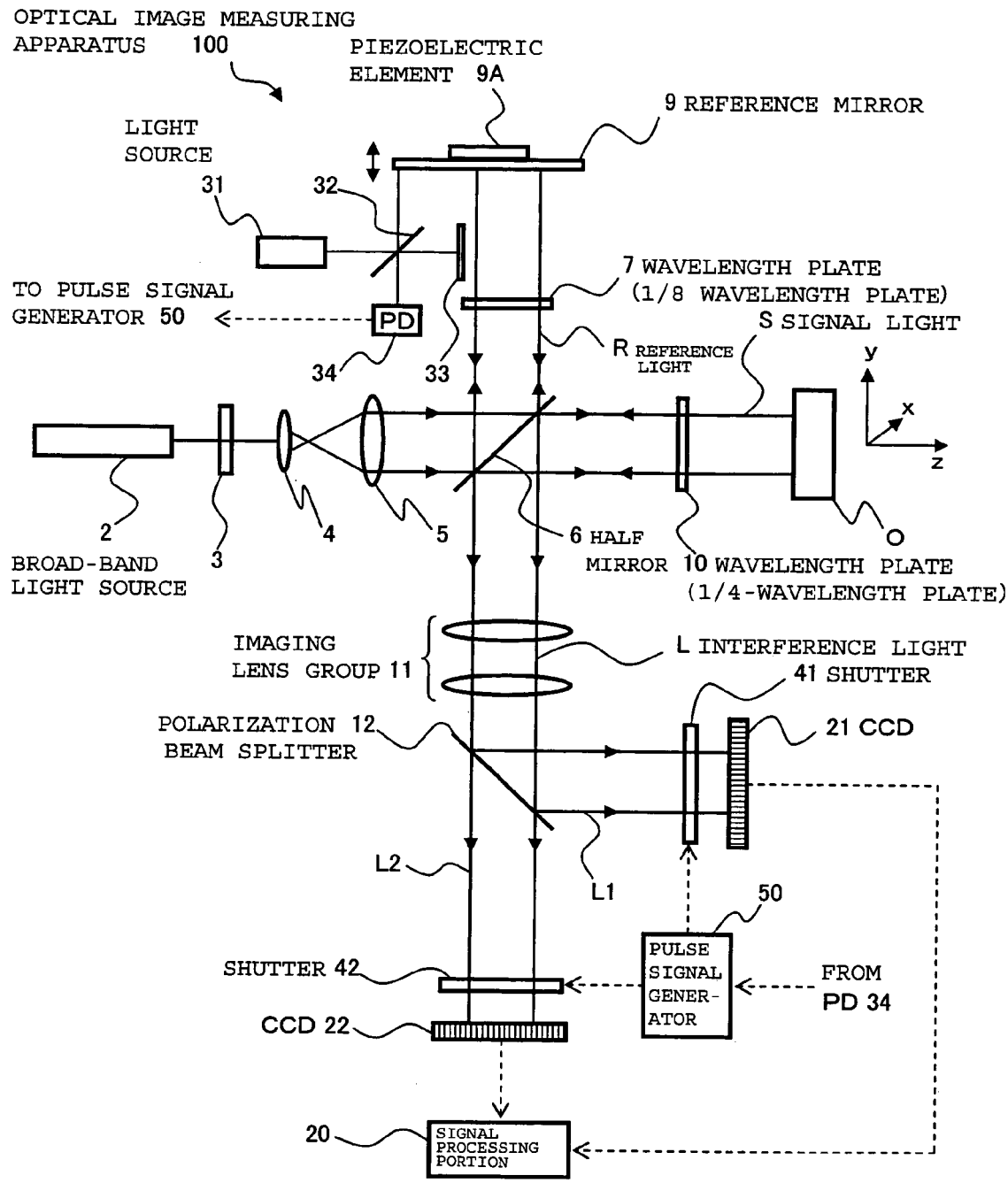
FIG. 4 is a schematic diagram showing an example of an optical image measuring apparatus according to a second embodiment of the present invention.

First, the optical image measuring apparatus according to this embodiment will be described. FIG. 4 illustrates a structural example of (mainly) an optical system of the optical image measuring apparatus according to this embodiment. In FIG. 4, the same reference symbols are provided to the same constituent portions as those in the first embodiment. Hereinafter, the detailed descriptions related to the same constituent portions as those in the first embodiment are omitted.

As in the first embodiment, an optical image measuring apparatus 100 shown in FIG. 4 includes the broad-band light source 2, the polarizing plate 3, the lenses 4 and 5, the half mirror 6, the wavelength plate (⅛-wavelength plate) 7, the reference mirror 9, the piezoelectric element 9A, the wavelength plate (¼-wavelength plate) 10, the imaging lens group 11, the polarization beam splitter 12, the signal processing portion 20, the CCDs 21 and 22, the laser light source 31, the beam splitter 32, the reflecting mirror 33, and the photo detector (PD) 34. The light source 2 is composed of a device capable of continuously generating low-coherent light, such as a SLD or a light emitting diode (LED).

As in the first embodiment, a frequency shifter composed of an optoelectronic modulator, an acoustooptic modulator, or the like may be provided on the optical path of the reference light R. More specifically, the frequency shifter may be provided immediately in front of the reference mirror 9.

The optical image measuring apparatus 100 according to this embodiment further includes shutters 41 and 42 (intensity modulating means) provided immediately in front of the CCDs 21 and 22, respectively. The shutters 41 and 42 periodically cut off the S-polarized light component L1 and the P-polarized light component L2, respectively. Each of the shutters 41 and 42 is, for example, a high-speed shutter such as a liquid crystal shutter. The liquid crystal shutter includes a liquid crystal panel for transmitting and cutting off light and a driver circuit for driving the liquid crystal panel in response to a pulse signal as described later to switch between light transmission and light cutoff.

It is not required that the shutters 41 and 42 be disposed immediately in front of the CCDs 21 and 22, respectively. The shutters 41 and 42 can be disposed at arbitrary positions on respective optical paths joining separation points of the S-polarized light component L1 and the P-polarized light component L2 of the interference light L which are separated by the polarization beam splitter 12 with the CCDs 21 and 22. That is, it is only necessary that the shutters 41 and 42 be disposed in positions in which the S-polarized light component L1 and the P-polarized light component L2 of the interference light L can be cut off and transmitted to change the amount of light received by each of the CCDs 21 and 22 between 0 and 100.

The intensity modulating means in the present invention, for modulating the intensities of the polarized light components of the interference light L is not limited to the shutters 41 and 42 for switching between light transmission and light cutoff. A structure for changing light transmittance may be used. For example, it is possible to apply a structure for switching a display state of the liquid crystal panel of the liquid crystal shutter between a state in which transmittance is 100% and a state in which transmittance is 50%.

The optical image measuring apparatus 100 further includes a pulse signal generator 50 (pulse signal generating means) for generating pulse signals for shutter driving and outputting the generated pulse signals to the shutters 41 and 42. The shutters 41 and 42 separately cut off and transmit the S-polarized light component L1 and the P-polarized light component L2 of the interference light L, respectively, in response to the pulse signals from the pulse signal generator 50 as timing signals.

The pulse signal generator 50 receives an electrical signal (having a frequency substantially equal to the beat frequency of the interference light L) outputted from the photo detector 34, generates pulse signals each having a frequency synchronized with the frequency of the electrical signal (for example, a frequency equal to that of the electrical signal), and outputs the generated pulse signals to the shutters 41 and 42. Therefore, the shutters 41 and 42 are operative to simultaneously cut off the S-polarized light component L1 and the P-polarized light component L2 at the frequency synchronized with (for, example, the frequency equal to) the beat frequency of the interference light L. Thus, the S-polarized light component L1 and the P-polarized light component L2 of the interference light L are simultaneously detected by the CCDs 21 and 22 at the frequency synchronized with the beat frequency of the interference light L. The CCDs 21 and 22 output the detection signals as described in the first embodiment to the signal processing portion 20. The signal processing portion 20 performs the same processing as that described in detail in the first embodiment based on the detection signals outputted from the CCDs 21 and 22 to form an image reflecting the birefringent property, of the object to be measured O and causes the monitor device (not shown) to display the image.

According to the optical image measuring apparatus 100 in this embodiment, as in the first embodiment, even when the image reflecting the birefringent property, of the object to be measured O is to be obtained over a wide range, the two-dimensional image (image on the xy-plane) of the object to be measured O in a certain depth region can be obtained at a time. Therefore, scanning with the signal light S in the xy-direction is unnecessary unlike a conventional case. Thus, the image reflecting the birefringent property, of the object to be measured O can be effectively measured in a short time. Even when a three-dimensional image or a one-dimensional image is to be formed, efficient and effective image processing can be executed as in the first embodiment.

MODIFIED EXAMPLE

In the above-mentioned optical image measuring apparatus 100, the shutters 41 and 42 are controlled so as to "simultaneously" cut off the S-polarized light component L1 and the P-polarized light component L2 at the frequency synchronized with the beat frequency of the interference light L in response to the pulse signals outputted from the pulse signal generator 50 based on the electrical signal from the photodetector 34. In the modified example described below, the S-polarized light component L1 and the P-polarized light component L2 are sampled by "changing open-and-close timings" of the shutters 41 and 42.

Figure 5:
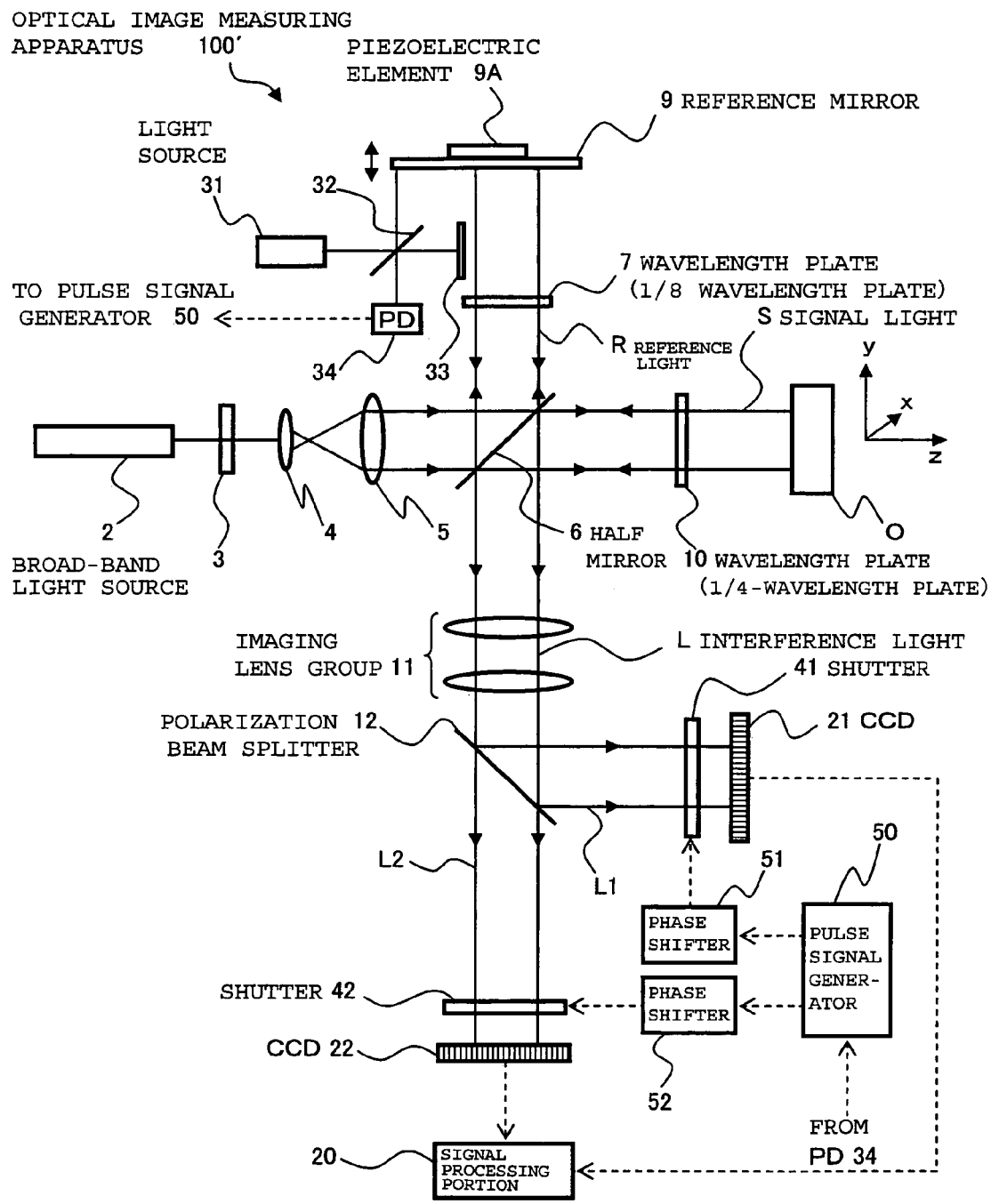
FIG. 5 is a schematic diagram showing a modified example of the optical image measuring apparatus according to the second embodiment of the present invention.

FIG. 5 illustrates an example showing a structure of an optical image measuring apparatus according to this modified example. An optical image measuring apparatus 100' shown in FIG. 5 has a structure similar to that of the optical image measuring apparatus 100 according to the second embodiment.

In order to control the operations of the shutters 41 and 42, the optical image measuring apparatus 100' in this modified example includes the pulse signal generator 50 and phase shifters 51 and 52 (phase difference applying means). The pulse signal generator 50 generates pulse signals for shutter driving based on the electrical signal outputted from the photo detector 34. The phase shifters 51 and 52 shift the phases of the pulse signals generated by the pulse signal generator 50 and output the pulse signals whose phases are shifted to each other to the shutters 41 and 42. The shutters 41 and 42 separately cut off and transmit the S-polarized light component L1 and the P-polarized light component L2 of the interference light L, respectively, in response to the pulse signals from the phase shifters 51 and 52 as timing signals.

The pulse signal generator 50 generates pulse signals each having a frequency synchronized with that of an electrical signal outputted from the photo detector 34 (for example, a frequency equal to that of the electrical signal) and outputs the generated pulse signals to the phase shifters 51 and 52. The phase shifters 51 and 52 shift the phases of the pulse signals relative to each other by a predetermined phase difference and output the pulse signals whose phases are shifted to each other to the shutters 41 and 42.

The phase difference which is applied between the two pulse signals by the phase shifters 51 and 52 is set to an arbitrary phase difference other than 180° ($\pi$), such as 90° ($\pi/2$). This is because, when the phase difference is set to 180° ($\pi$), it becomes equal to a phase difference applied between the S-polarized light component L1 and the P-polarized light component L2 by the wavelength plate 7 located on the optical path of the reference light R.

It is unnecessary to provide the phase shifter for each of the shutters 41 and 42. The phase shifter may be provided for only one of the shutters 41 and 42. For example, it is possible to employ a structure in which the phase shifter is disposed for not the shutter 41 but the shutter 42 or a reverse-structure.

The shutters 41 and 42 are driven based on the pulse signals whose phases are shifted relative to each other and repeat the open-and-close operation at a frequency equal to that of the pulse signals. At this time, the shutters 41 and 42 are opened and closed based on a time difference corresponding to the phase difference applied between the pulse signals by the phase shifters 51 and 52. Therefore, the CCDs 21 and 22 receive the S-polarized light component L1 and the P-polarized light component L2, respectively, at the frequency synchronized with the beat frequency of the interference light L based on a predetermined time difference. The CCDs 21 and 22 output the detection signals as described in the first embodiment to the signal processing portion 20. The signal processing portion 20 performs the same processing as that in the first embodiment based on the detection signals outputted from the CCDs 21 and 22 to form an image of the object to be measured O.

According to the optical image measuring apparatus 100' in this modified example, as in the second embodiment, the image reflecting the birefringent property, of the object to be measured O can be obtained over a wide range without scanning with the signal light S unlike a conventional case. Thus, effective image measurement can be efficiently performed.

Third Embodiment

An optical image measuring apparatus according to a third embodiment of the present invention will be described. In this embodiment, the interference light beams produced based on the continuous light beam are sampled using the shutters as in the second embodiment. In the optical image measuring apparatus according to this embodiment, in order to apply the phase difference between the detected S-polarized light component L1 and the detected P-polarized light component L2 of the interference light, the shutters which are disposed on the optical paths of the polarized light components and opened and closed based on a time difference corresponding to the phase difference to be applied by the wavelength plate is used instead of the wavelength plate (reference numeral 7) disposed on the optical path of the reference light.

Figure 6:
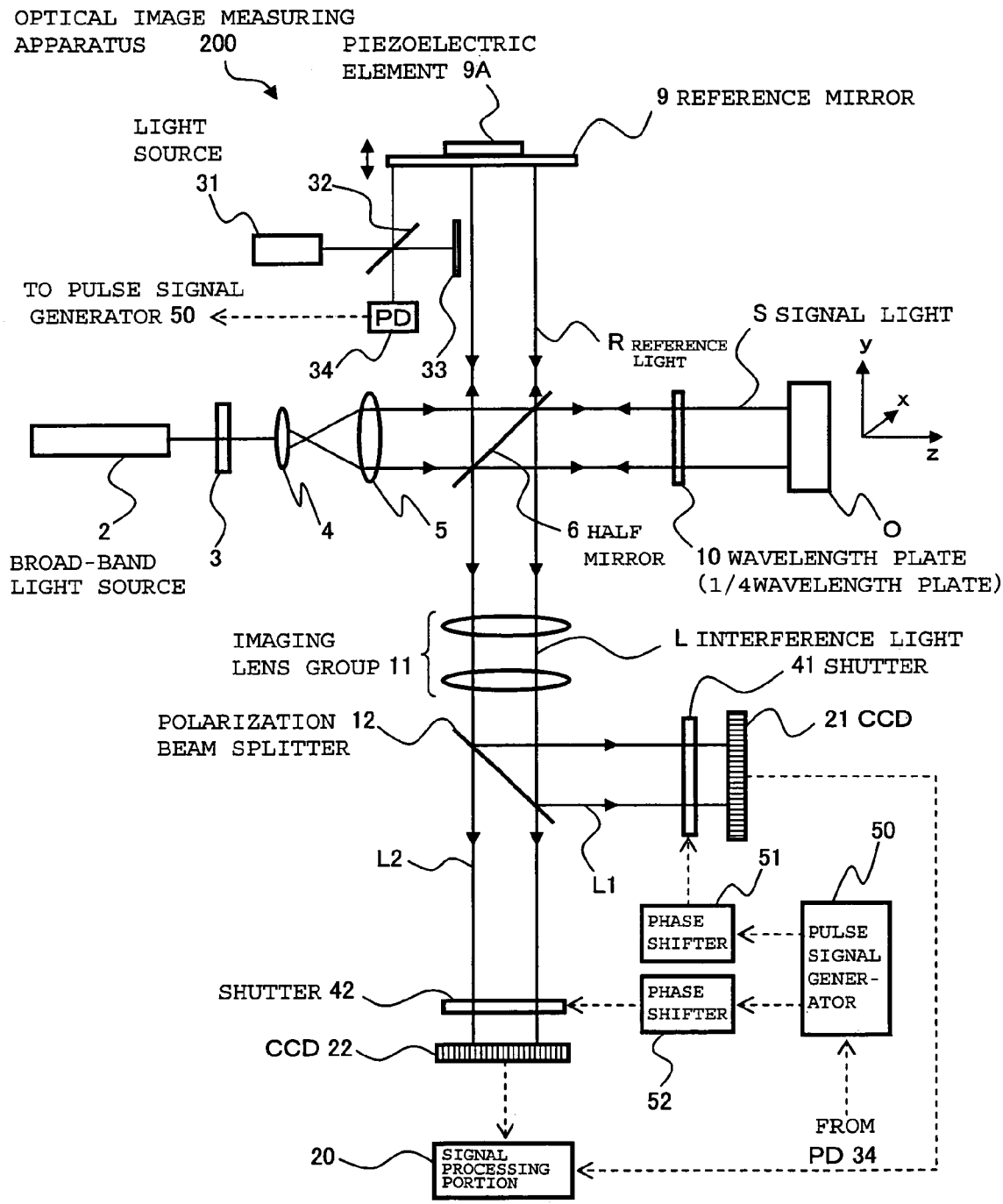
FIG. 6 is a schematic diagram showing an example of an optical image measuring apparatus according to a third embodiment of the present invention.
Figure 7:
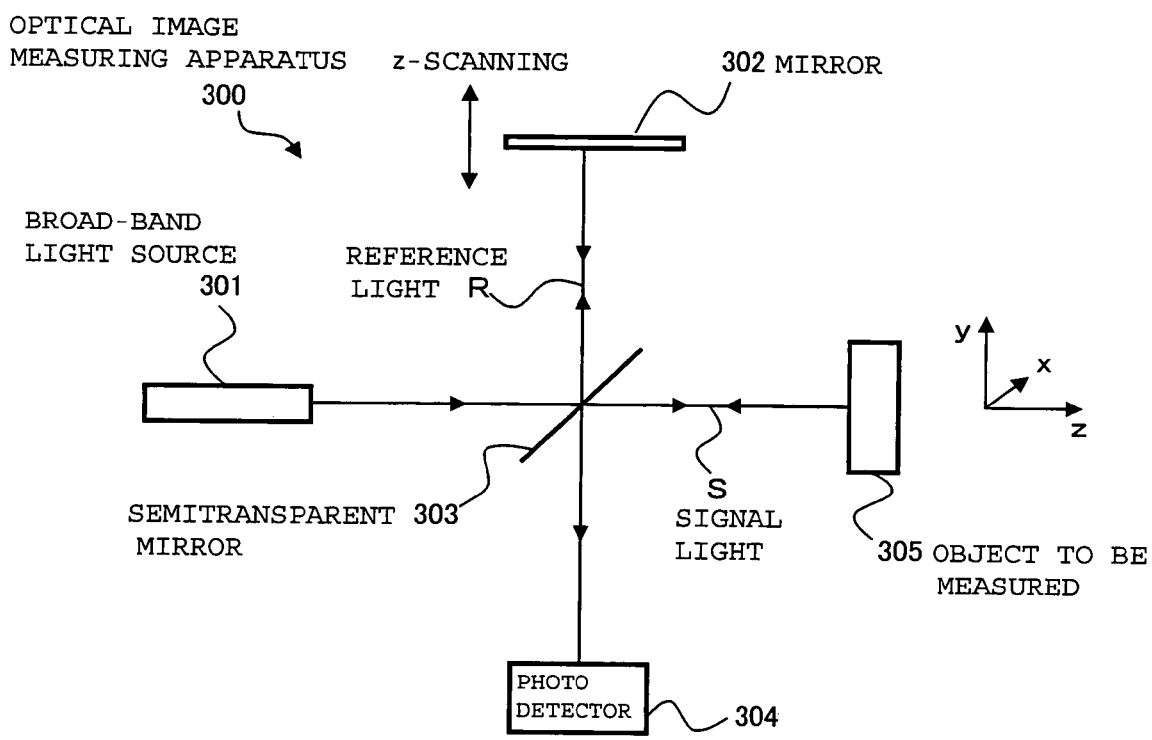
FIG. 7 is a schematic diagram showing a conventional optical image measuring apparatus.
Figure 8:
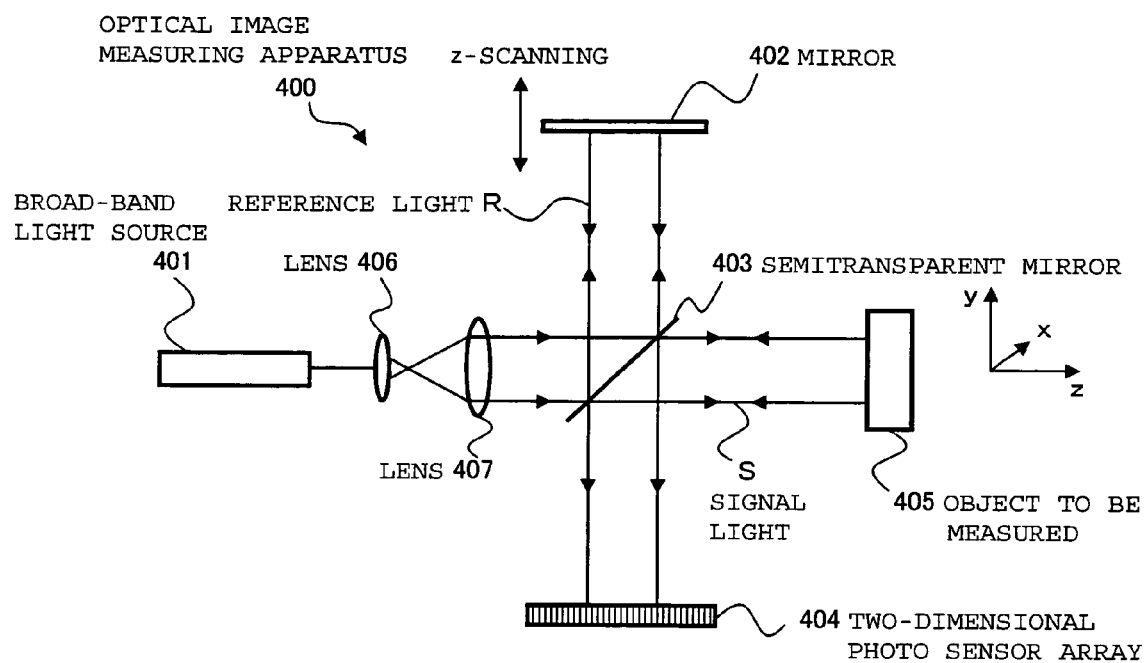
FIG. 8 is a schematic diagram showing a conventional optical image measuring apparatus.

As in the second embodiment, an optical image measuring apparatus 200 shown in FIG. 6 includes the broad-band light source 2, the polarizing plate 3, the lenses 4 and 5, the half mirror 6, the reference mirror 9, the piezoelectric element 9A, the wavelength plate (¼-wavelength plate) 10, the imaging lens group 11, the polarization beam splitter 12, the signal processing portion 20, the CCDs 21 and 22, the laser light source 31, the beam splitter 32, the reflecting mirror 33, the photodetector (PD) 34, the shutters 41 and 42 (intensity modulating means), the pulse signal generator 50 (pulse signal generating means), and the phase shifters 51 and 52 (phase difference applying means). The light source 2 continuously generates low-coherent light. A frequency shifter composed of an optoelectronic modulator, an acoustooptic modulator, or the like may be provided on the optical path of the reference light R.

The pulse signal generator 50 generates pulse signals each having a frequency synchronized with that of an electrical signal outputted from the photo detector 34 (for example, a frequency equal to that of the electrical signal) and outputs the generated pulse signals to the phase shifters 51 and 52. The phase shifters 51 and 52 shift the phases of the pulse signals relative to each other by a predetermined phase difference and output the pulse signals whose phases are shifted to each other to the shutters 41 and 42.

The phase difference applied between the two pulse signals by the phase shifters 51 and 52 is set to a phase difference equal to the phase difference to be applied between the S-polarized light component L1 and the P-polarized light component L2 of the interference light L by the wavelength plate 7 disposed on the optical path of the reference light R in the first and second embodiments, that is, 180° ($\pi$). Therefore, for example, the phase shifter 51 delays the phase of the pulse signal from the pulse signal generator 50 by 90° and the phase shifter 52 advances the phase of the pulse signal from the pulse signal generator 50 by 90°. For example, in the case where a target phase difference is applied by a single phase shifter, such as the case where the phase of the pulse signal is advanced by 180° by the phase shifter 51, it is unnecessary to provide the phase shifter for each of the shutters 41 and 42. It is only necessary to provide the phase shifter for one of the shutters 41 and 42.

The shutters 41 and 42 are driven based on the pulse signals from the phase shifters 51 and 52 and repeat the open-and-close operation at the frequency equal to that of the pulse signals. At this time, the shutters 41 and 42 are opened and closed based on the time difference corresponding to the phase difference applied between the pulse signals by the phase shifters 51 and 52 (phase difference of 180° in the beat of the interference light L). Therefore, the S-polarized light component L1 and the P-polarized light component L2 are received by the CCDs 21 and 22, respectively, at the frequency synchronized with the beat frequency of the interference light L based on the time difference corresponding to the phase difference to be applied by the wavelength plate 7. The CCDs 21 and 22 output the detection signals as described in the first and second embodiments to the signal processing portion 20. The signal processing portion 20 performs the same processing as that in the first embodiment based on the detection signals outputted from the CCDs 21 and 22 to form an image of the object to be measured O.

According to the optical image measuring apparatus 200 in this embodiment, as in the first and second embodiments, the image reflecting the birefringent property, of the object to be measured O can be obtained over a wide range without scanning with the signal light S. Thus, effective image measurement can be efficiently performed.

OTHER MODIFIED EXAMPLES

The above-mentioned detailed embodiments are merely examples for embodying the optical image measuring apparatus according to the present invention. Therefore, arbitrary modifications can be made without departing from the spirit of the present invention.

For example, the method of modulating the intensity of the light beam in the first embodiment is not limited to the above-mentioned method of pulse-driving the light source and the above-mentioned method of periodically cutting off the light beam using the shutter, and thus an arbitrary method can be applied. For example, the intensity of the light beam can be modulated by periodically inserting or removing a neutral density filter onto or from the optical path of the light beam.

An arbitrary element instead of the piezoelectric element can be applied to move the reference object (reference mirror).

In the first embodiment, it is only necessary that the frequency for the intensity modulation of the light beam be synchronized with the beat frequency of the interference light. Therefore, an arbitrary structure can be employed to realize the synchronization. Similarly, in each of the second and third embodiments, it is only necessary that the frequency for the intensity modulation of the interference light which is performed by the intensity modulating means (shutter) be synchronized with the beat frequency of the interference light. Therefore, an arbitrary structure can be employed to realize the synchronization. For example, when an optical image measuring apparatus in which the beat frequency of the interference light (relative frequency difference between the signal light and the reference light) is maintained constant is to be constructed, it is possible to set an intensity modulation frequency for each of the light beam and the interference light to a predetermined value.

What is claimed is:

1. An optical image measuring apparatus, comprising:
   light beam outputting means for outputting a light beam whose intensity is periodically modulated;
   beam diameter increasing means for increasing a beam diameter of the light beam;
   linear polarization means for converting a polarization characteristic of the light beam to linear polarization;
   light beam dividing means for dividing the light beam whose beam diameter is increased and polarization characteristic is converted to the linear polarization into signal light propagating to an object to be measured and reference light propagating to a reference object;
   reference light polarizing means for converting a polarization characteristic of the reference light which is linearly polarized light;
   signal light polarizing means for converting a polarization characteristic of the signal light which is linearly polarized light before the signal light propagates through the object to be measured and converting to linear polarization the polarization characteristic of the signal light after the signal light propagates through the object to be measured;
   frequency shifting means for shifting a frequency of the signal light and a frequency of the reference light relative to each other;
   superimposing means for superimposing the reference light whose polarization characteristic is converted by the reference light polarizing means and the signal light which is converted to linearly polarized light by the signal light polarizing means on each other to produce interference light, the frequency of the signal light and the frequency of the reference light being shifted relative to each other by the frequency shifting means;
   interference light separating means for separating a plurality of polarized light components which are different from each other from the produced interference light;
   detecting means for receiving the polarized light components separated from the interference light and outputting a detection signal including intensity change information of each of the polarized light components; and
   signal processing means for forming an image reflecting a birefringent property, of the object to be measured based on the intensity change information of each of the polarized light components included in the outputted detection signal.

2. An optical image measuring apparatus according to claim 1, wherein the linear polarization means converts the light beam to linearly polarized light in an angle direction of 45° relative to an x-axis and a y-axis of an xy-plane orthogonal to a propagating direction of the light beam, and
   the reference light polarizing means converts the reference light which is the linearly polarized light in the angle direction of 45° to circularly polarized light.

3. An optical image measuring apparatus according to claim 2, wherein the linear polarization means comprises a polarizing plate for transmitting an oscillation component of the light beam in the angle direction of 45°.

4. An optical image measuring apparatus according to claim 3, wherein the interference light separating means separates a P-polarized light component and an S-polarized light component which are orthogonal to each other from the interference light.

5. An optical image measuring apparatus according to claim 4, wherein the light beam outputting means comprises:
   pulse generating means for generating a pulse signal having a frequency synchronized with frequency shift caused by the frequency shifting means; and
   a light source for outputting a pulsed light beam, which is driven based on the pulse signal.

6. An optical image measuring apparatus according to claim 5, wherein the pulse generating means comprises:
   a laser light source for emitting laser light;
   an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;
   auxiliary detection means for detecting the produced auxiliary interference light and outputting an electrical signal having a frequency substantially equal to a beat frequency of the detected auxiliary interference light; and
   light source driving means for generating the pulse signal having the frequency synchronized with the frequency of the electrical signal outputted from the auxiliary detection means and outputting the generated pulse signal to the light source.

7. An optical image measuring apparatus according to claim 4, wherein the light beam means comprises:
   a light source for emitting a continuous light beam; and
   shutter means for periodically cutting off the emitted continuous light beam.

8. An optical image measuring apparatus according to claim 7, wherein the light beam means comprises:
   a laser light source for emitting laser light;
   an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;
   auxiliary detection means for detecting the produced auxiliary interference light and outputting an electrical signal having a frequency substantially equal to a beat frequency of the auxiliary interference light; and shutter driving means for generating a pulse signal having a frequency synchronized with the frequency of the electrical signal outputted from the auxiliary detection means and outputting the generated pulse signal to the shutter means, and wherein the shutter means is driven based on the pulse signal outputted from the shutter driving means and periodically cuts off the continuous light beam emitted from the light source.

9. An optical image measuring apparatus according to claim 2, wherein the light beam dividing means and the superimposing means integrally compose a half mirror tilted relative to an optical path of the light beam outputted from the light beam outputting means, an optical path of the signal light, and an optical path of the reference light, and the reference light polarizing means comprises a ⅛-wavelength plate located between the half mirror and the reference object.

10. An optical image measuring apparatus according to claim 9, wherein the linear polarization means comprises a polarizing plate for transmitting an oscillation component of the light beam in the angle direction of 45°.

11. An optical image measuring apparatus according to claim 10, wherein the interference light separating means separates a P-polarized light component and an S-polarized light component which are orthogonal to each other from the interference light.

12. An optical image measuring apparatus according to claim 11, wherein the light beam outputting means comprises:

pulse generating means for generating a pulse signal having a frequency synchronized with frequency shift caused by the frequency shifting means; and a light source for outputting a pulsed light beam, which is driven based on the pulse signal.

13. An optical image measuring apparatus according to claim 12, wherein the pulse generating means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the detected auxiliary interference light; and light source driving means for generating the pulse signal having the frequency synchronized with the frequency of the electrical signal outputted from the auxiliary detection means and outputting the generated pulse signal to the light source.

14. An optical image measuring apparatus according to claim 11, wherein the light beam means comprises:

a light source for emitting a continuous light beam; and shutter means for periodically cutting off the emitted continuous light beam.

15. An optical image measuring apparatus according to claim 14, wherein the light beam means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the auxiliary interference light; and shutter-driving means for generating a pulse signal having a frequency synchronized with the frequency of the electrical signal outputted from the auxiliary detection means and outputting the generated pulse signal to the shutter means, and wherein the shutter means is driven based on the pulse signal outputted from the shutter driving means and periodically cuts off the continuous light beam emitted from the light source.

16. An optical image measuring apparatus according to claim 1, wherein the linear polarization means converts the light beam to linearly polarized light in an angle direction of 45° relative to an x-axis and a y-axis of an xy-plane orthogonal to a propagating direction of the light beam, and the signal light polarizing means converts to circularly polarized light the signal light which is the linearly polarized light in the angle direction of 45° before the signal light propagates through the object to be measured and converts to linearly polarized light the signal light which is the circularly polarized light after the signal light propagates through the object to be measured.

17. An optical image measuring apparatus according to claim 16, wherein the linear polarization means converts the light beam to linearly polarized light in an angle direction of 45° relative to an x-axis and a y-axis of an xy-plane orthogonal to a propagating direction of the light beam, and the reference light polarizing means converts the reference light which is the linearly polarized light in the angle direction of 45° to circularly polarized light.

18. An optical image measuring apparatus according to claim 17, wherein the linear polarization means comprises a polarizing plate for transmitting an oscillation component of the light beam in the angle direction of 45°.

19. An optical image measuring apparatus according to claim 18, wherein the interference light separating means separates a P-polarized light component and an S-polarized light component which are orthogonal to each other from the interference light.

20. An optical image measuring apparatus according to claim 19, wherein the light beam outputting means comprises:

pulse generating means for generating a pulse signal having a frequency synchronized with frequency shift caused by the frequency shifting means; and a light source for outputting a pulsed light beam, which is driven based on the pulse signal.

21. An optical image measuring apparatus according to claim 20, wherein the pulse generating means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the detected auxiliary interference light; and light source driving means for generating the pulse signal having the frequency synchronized with the frequency of the electrical signal outputted from the auxiliary detection means and outputting the generated pulse signal to the light source.

22. An optical image measuring apparatus according to claim 19, wherein the light beam means comprises:

a light source for emitting a continuous light beam; and shutter means for periodically cutting off the emitted continuous light beam.

23. An optical image measuring apparatus according to claim 22, wherein the light beam means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the auxiliary interference light; and shutter driving means for generating a pulse signal having a frequency synchronized with the frequency of the electrical signal outputted from the auxiliary detection means and outputting the generated pulse signal to the shutter means, and wherein the shutter means is driven based on the pulse signal outputted from the shutter driving means and periodically cuts off the continuous light beam emitted from the light source.

24. An optical image measuring apparatus according to claim 17, wherein the light beam dividing means and the superimposing means integrally compose a half mirror tilted relative to an optical path of the light beam outputted from the light beam outputting means, an optical path of the signal light, and an optical path of the reference light, and the reference light polarizing means comprises a ⅛-wavelength plate located between the half mirror and the reference object.

25. An optical image measuring apparatus according to claim 24, wherein the linear polarization means comprises a polarizing plate for transmitting an oscillation component of the light beam in the angle direction of 45°.

26. An optical image measuring apparatus according to claim 25, wherein the interference light separating means separates a P-polarized light component and an S-polarized light component which are orthogonal to each other from the interference light.

27. An optical image measuring apparatus according to claim 26, wherein the light beam outputting means comprises:

pulse generating means for generating a pulse signal having a frequency synchronized with frequency shift caused by the frequency shifting means; and a light source for outputting a pulsed light beam, which is driven based on the pulse signal.

28. An optical image measuring apparatus according to claim 27, wherein the pulse generating means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the detected auxiliary interference light; and light source driving means for generating the pulse signal having the frequency synchronized with the frequency of the electrical signal outputted from the auxiliary detection means and outputting the generated pulse signal to the light source.

29. An optical image measuring apparatus according to claim 26, wherein the light beam means comprises:

a light source for emitting a continuous light beam; and shutter means for periodically cutting off the emitted continuous light beam.

30. An optical image measuring apparatus according to claim 29, wherein the light beam means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the auxiliary interference light; and shutter driving means for generating a pulse signal having a frequency synchronized with the frequency of the electrical signal outputted from the auxiliary detection means and outputting the generated pulse signal to the shutter means, and wherein the shutter means is driven based on the pulse signal outputted from the shutter driving means and periodically cuts off the continuous light beam emitted from the light source.

31. An optical image measuring apparatus according to claim 2, wherein the light beam dividing means and the superimposing means integrally compose a half mirror tilted relative to an optical path of the light beam outputted from the light beam outputting means, an optical path of the signal light, and an optical path of the reference light, and the signal light polarizing means comprises a ¼-wavelength plate located between the half mirror and the object to be measured.

32. An optical image measuring apparatus according to claim 31, wherein the linear polarization means converts the light beam to linearly polarized light in an angle direction of 45° relative to an x-axis and a y-axis of an xy-plane orthogonal to a propagating direction of the light beam, and the reference light polarizing means converts the reference light which is the linearly polarized light in the angle direction of 45° to circularly polarized light.

33. An optical image measuring apparatus according to claim 32, wherein the linear polarization means comprises a polarizing plate for transmitting an oscillation component of the light beam in the angle direction of 45°.

34. An optical image measuring apparatus according to claim 33, wherein the interference light separating means separates a P-polarized light component and an S-polarized light component which are orthogonal to each other from the interference light.

35. An optical image measuring apparatus according to claim 34, wherein the light beam outputting means comprises:
pulse generating means for generating a pulse signal having a frequency synchronized with frequency shift caused by the frequency shifting means; and
a light source for outputting a pulsed light beam, which is driven based on the pulse signal.

36. An optical image measuring apparatus according to claim 35, wherein the pulse generating means comprises:
a laser light source for emitting laser light;
an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;
auxiliary detection means for detecting the produced auxiliary interference light and outputting an electrical signal having a frequency substantially equal to a beat frequency of the detected auxiliary interference light; and
light source driving means for generating the pulse signal having the frequency synchronized with the frequency of the electrical signal outputted from the auxiliary detection means and outputting the generated pulse signal to the light source.

37. An optical image measuring apparatus according to claim 34, wherein the light beam means comprises:
a light source for emitting a continuous light beam; and
shutter means for periodically cutting off the emitted continuous light beam.

38. An optical image measuring apparatus according to claim 37, wherein the light beam means comprises:
a laser light source for emitting laser light;
an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;
auxiliary detection means for detecting the produced auxiliary interference light and outputting an electrical signal having a frequency substantially equal to a beat frequency of the auxiliary interference light; and
shutter driving means for generating a pulse signal having a frequency synchronized with the frequency of the electrical signal outputted from the auxiliary detection means and outputting the generated pulse signal to the shutter means, and
wherein the shutter means is driven based on the pulse signal outputted from the shutter driving means and periodically cuts off the continuous light beam emitted from the light source.

39. An optical image measuring apparatus according to claim 32, wherein the light beam dividing means and the superimposing means integrally compose a half mirror tilted relative to an optical path of the light beam outputted from the light beam outputting means, an optical path of the signal light, and an optical path of the reference light, and
the reference light polarizing means comprises a ⅛-wavelength plate located between the half mirror and the reference object.

40. An optical image measuring apparatus according to claim 39, wherein the linear polarization means comprises a polarizing plate for transmitting an oscillation component of the light beam in the angle direction of 45°.

41. An optical image measuring apparatus according to claim 40, wherein the interference light separating means separates a P-polarized light component and an S-polarized light component which are orthogonal to each other from the interference light.

42. An optical image measuring apparatus according to claim 41, wherein the light beam outputting means comprises:
pulse generating means for generating a pulse signal having a frequency synchronized with frequency shift caused by the frequency shifting means; and
a light source for outputting a pulsed light beam, which is driven based on the pulse signal.

43. An optical image measuring apparatus according to claim 42, wherein the pulse generating means comprises:
a laser light source for emitting laser light;
an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;
auxiliary detection means for detecting the produced auxiliary interference light and outputting an electrical signal having a frequency substantially equal to a beat frequency of the detected auxiliary interference light; and
light source driving means for generating the pulse signal having the frequency synchronized with the frequency of the electrical signal outputted from the auxiliary detection means and outputting the generated pulse signal to the light source.

44. An optical image measuring apparatus according to claim 41, wherein the light beam means comprises:
a light source for emitting a continuous light beam; and
shutter means for periodically cutting off the emitted continuous light beam.

45. An optical image measuring apparatus according to claim 44, wherein the light beam means comprises:
a laser light source for emitting laser light;
an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the auxiliary interference light; and shutter driving means for generating a pulse signal having a frequency synchronized with the frequency of the electrical signal outputted from the auxiliary detection means and outputting the generated pulse signal to the shutter means, and wherein the shutter means is driven based on the pulse signal outputted from the shutter driving means and periodically cuts off the continuous light beam emitted from the light source.

46. An optical image measuring apparatus according to claim 31, wherein the light beam outputting means comprises:

pulse generating means for generating a pulse signal having a frequency synchronized with frequency shift caused by the frequency shifting means; and a light source for outputting a pulsed light beam, which is driven based on the pulse signal.

47. An optical image measuring apparatus according to claim 46, wherein the pulse generating means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the detected auxiliary interference light; and light source driving means for generating the pulse signal having the frequency synchronized with the frequency of the electrical signal outputted from the auxiliary detection means and outputting the generated pulse signal to the light source.

48. An optical image measuring apparatus according to claim 31, wherein the light beam means comprises:

a light source for emitting a continuous light beam; and shutter means for periodically cutting off the emitted continuous light beam.

49. An optical image measuring apparatus according to claim 48, wherein the light beam means comprises:

a laser light source for emitting laser light;

an auxiliary optical interference system for dividing the emitted laser light into first laser light propagating to the frequency shifting means and second laser light propagating to a reflecting mirror which is fixedly located and superimposing the first laser light which is subjected to the frequency shift and the second laser light reflected on the reflecting mirror on each other to produce auxiliary interference light;

auxiliary detection means for detecting the produced auxiliary interference light and outputting an electrical signal having a frequency substantially equal to a beat frequency of the auxiliary interference light; and shutter driving means for generating a pulse signal having a frequency synchronized with the frequency of the electrical signal outputted from the auxiliary detection means and outputting the generated pulse signal to the shutter means, and wherein the shutter means is driven based on the pulse signal outputted from the shutter driving means and periodically cuts off the continuous light beam emitted from the light source.

* * * * *